US012762877B2

(12) United States Patent
Holmsten et al.

(10) Patent No.: US 12,762,877 B2
(45) **Date of Patent: *Oct. 13, 2026**

(54) COMPUTER-IMPLEMENTED SEGMENTED NUMERAL CHARACTER RECOGNITION AND READER

(71) Applicant: REDIMD, LLC, Houston, TX (US)

(72) Inventors: Walter Holmsten, Houston, TX (US); Malcolm Edward Storey, Houston, TX (US); Aakash L. Gupta, Sanpada Navi (IN)

(73) Assignee: REDIMD, LLC, Houston, TX (US)

( * ) Notice: Subject to any disclaimer, the term of this patent is extended or adjusted under 35 U.S.C. 154(b) by 172 days.

This patent is subject to a terminal disclaimer.

(21) Appl. No.: 18/669,750

(22) Filed: May 21, 2024

(65) Prior Publication Data

US 2024/0304014 A1 Sep. 12, 2024

Related U.S. Application Data

(63) Continuation of application No. PCT/US2022/081318, filed on Dec. 9, 2022, and a (Continued)

(51) Int. Cl.

*G06V 30/19* (2022.01)
*G06V 10/94* (2022.01)

(Continued)

(52) U.S. Cl.

CPC ...... *G06V 30/19147* (2022.01); *G06V 10/945* (2022.01); *G06V 20/62* (2022.01);

(Continued)

(58) Field of Classification Search

CPC ....... G06V 30/19147; G06V 30/19007; G06V 30/19107; G06V 20/62; G06V 30/1916;

(Continued)

(56) References Cited

U.S. PATENT DOCUMENTS 8,554,195 B2 * 10/2013 Rao ........................ H04L 51/214 455/550.1
10,383,794 B2 8/2019 Khalid (Continued)

FOREIGN PATENT DOCUMENTS

KR 102150200 B1 8/2020

OTHER PUBLICATIONS

Blood Glucose Meter Guide, Guide to Blood Glucose Meters, Blood Glucose Monitors, pp. 1-36, URL: <https://www.diabetes.co.uk/diabetes_care/blood_glucose_monitor_guide.html>, retrieved from the Internet Mar. 16, 2022.

(Continued)

*Primary Examiner* — Gregory M Desire

(74) *Attorney, Agent, or Firm* — Vorys, Sater, Seymour and Pease, LLP; Michael Messinger

(57) ABSTRACT

Computer-implemented methods, systems and devices having segmented numeral character recognition. In an embodiment, users may take digital pictures of a seven-segment display on a sensor device. For example, a user at a remote location may use a digital camera to capture a digital image of a seven-segment display on a sensor device. Captured images of a seven-segment display may then be sent or uploaded over a network to a remote health management system. The health care management system includes a reader that processes the received images to determine sensor readings representative of the values output on the seven-segment displays of the remote sensor devices. Machine learning and OCR are used to identify numeric characters in images associated with seven-segment displays. In this way, a remote heath management system can obtain sensor readings from remote locations when users only have access to sensor devices with seven-segment displays.

13 Claims, 17 Drawing Sheets
(4 of 17 Drawing Sheet(s) Filed in Color)

Related U.S. Application Data continuation-in-part of application No. PCT/US2022/074460, filed on Aug. 3, 2022, said application No. PCT/US2022/081318 is a continuation of application No. 17/657,702, filed on Apr. 1, 2022, now Pat. No. 11,430,236, said application No. PCT/US2022/074460 is a continuation of application No. 17/657,702, filed on Apr. 1, 2022, now Pat. No. 11,430,236.

(60) Provisional application No. 63/287,731, filed on Dec. 9, 2021.

(51) Int. Cl.

| | |
|---|---|
| ***G06V 20/62*** | (2022.01) |
| ***G06V 30/146*** | (2022.01) |
| ***G16H 30/20*** | (2018.01) |
| ***G16H 40/67*** | (2018.01) |

(52) U.S. Cl.

CPC ...... *G06V 30/147* (2022.01); *G06V 30/19007* (2022.01); *G06V 30/19107* (2022.01); *G06V 30/1916* (2022.01); *G16H 30/20* (2018.01); *G16H 40/67* (2018.01); *G06V 2201/02* (2022.01)

(58) Field of Classification Search

CPC ............... G06V 30/147; G06V 10/945; G06V 2201/02; G16H 40/67; G16H 30/20

See application file for complete search history.

(56) References Cited

U.S. PATENT DOCUMENTS

| | | | | |
|---|---|---|---|---|
| 10,546,103 | B2 | 1/2020 | Ohnemus et al. | |
| 11,081,232 | B2 | 8/2021 | Aysin et al. | |
| 11,164,045 | B2 * | 11/2021 | Paik | G16H 15/00 |
| 11,430,236 | B1 | 8/2022 | Holmsten et al. | |
| 2009/0192813 | A1 | 7/2009 | Gejdos et al. | |
| 2016/0378921 | A1 | 12/2016 | Ohnemus et al. | |
| 2020/0273558 | A1 * | 8/2020 | Yousfi | G16H 30/20 |

OTHER PUBLICATIONS

US Blood Pressure Validated Device Listing (VDL), Validate BP, pp. 1-20, URL: <https://www.validatebp.org/?f=showall>, retrieved from the Internet Mar. 16, 2022.

GitHub, facebookresearch, Detectron, FAIR's research platform for object detection research, implementing popular algorithms like Mask R-CNN and RetinaNet, pp. 1-5, URL: <https://github.com/facebookresearch/detectron#readme>, retrieved from the Internet Mar. 21, 2022.

Jia Deng, Wei Dong, Richard Socher, Li-Jia Li, Kai Li, and Li Fei-Fei. Imagenet: A large-scale hierarchical image database. In 2009 IEEE Conference on Computer Vision and Pattern Recognition, pp. 248-255, 2009.

Li Deng. The mnist database of handwritten digit images for machine learning research [best of the web]. IEEE Signal Processing Magazine, 29(6):141-142, 2012.

Terrance DeVries and Graham W Taylor. Improved regularization of convolutional neural networks with cutout. arXiv preprint arXiv:1708.04552, 2017 (8 pages).

E Finnegan, M Villarroel, C Velardo, and L Tarassenko. Automated method for detecting and reading seven-segment digits from images of blood glucose metres and blood pressure monitors. Journal of medical engineering & technology, 43(6):341-355, 2019.

Soumyadip Ghosh and Suprosanna Shit. A low cost data acquisition system from digital display instruments employing image processing technique. In 2014 International Conference on Advances in Computing, Communications and Informatics (ICACCI), pp. 1065-1068. IEEE, 2014.

Rakhi P Ghugardare, Sandip P Narote, P Mukherji, and Prathamesh M Kulkarni. Optical character recognition system for seven segment display images of measuring instruments. In TENCON 2009—2009 IEEE Region 10 Conference, pp. 1-6. IEEE, 2009.

Karthick Kanagarathinam and Kavaskar Sekar. Text detection and recognition in raw image dataset of seven segment digital energy meter display. Energy Reports, 5:842-852, 2019.

Prachi H Kulkarni and Pratik D Kute. Optical numeral recognition algorithm for seven segment display. In 2016 Conference on Advances in Signal Processing (CASP), pp. 397-401. IEEE, 2016.

Muralindran Mariappan, Vigneswaran Ramu, Thayabaren Ganesan, Brendan Khoo, and Ku-marheshan Vellian. Virtual medical instrument for otorob based on labview for acquiring multiple medical instrument lcd reading using optical charcater recognition. In Proceedings from the International Conference on Biomedical Engineering and Technology (IPCBEE), vol. 11, pp. 70-74, 2011.

Shaoqing Ren, Kaiming He, Ross Girshick, and Jian Sun. Faster r-cnn: Towards real-time object detection with region proposal networks, 2016 (14 pages).

Connor Shorten and Taghi M. Khoshgoftaar, A survey on Image Data Augmentation for Deep Learning, Journal of Big Data, pp. 1-48, 2019.

Tuomas Savolainen, Daniel Keith Whiter, and Noora Partamies. Automatic segmentation and classification of seven-segment display digits on auroral images. Geoscientific Instrumentation, Methods and Data Systems, 5(2):305-314, 2016.

Varun N Shenoy and Oliver O Aalami. Utilizing smartphone-based machine learning in medical monitor data collection: seven segment digit recognition. In AMIA Annual Symposium Proceedings, vol. 2017, pp. 1564-1570. American Medical Informatics Association, 2017.

Hongyi Zhang, Moustapha Cisse, Yann N. Dauphin, and David Lopez-Paz. mixup: Beyond empirical risk minimization. International Conference on Learning Representations, 2018 (13 pages).

Sangdoo Yun, Dongyoon Han, Seong Joon Oh, Sanghyuk Chun, Junsuk Choe, and Youngjoon Yoo. Cutmix: Regularization strategy to train strong classifiers with localizable features. In International Conference on Computer Vision (ICCV), pp. 6023-6032, 2019.

International Search Report filed in corresponding PCT Application No. PCT/US2022/074460; dated Nov. 14, 2022; 3 pages.

Written Opinion filed in corresponding PCT Application No. PCT/US2022/074460; dated Nov. 14, 2022; 5 pages.

International Search Report filed in corresponding PCT Application No. PCT/US2022/081318; dated Apr. 3, 2023; 4 pages.

Written Opinion filed in corresponding PCT Application No. PCT/US2022/081318; dated Apr. 3, 2023; 5 pages.

International Preliminary Report on Patentability filed in corresponding PCT application No. PCT/US2022/081318, dated Jun. 5, 2024, 6 pages.

International Preliminary Report on Patentability filed in corresponding PCT application No. PCT/US2022/074460, dated Jun. 5, 2024, 6 pages.

* cited by examiner

SAMPLE IMAGE PROCESSED VIA AWS REKOGNITION API - NO DIGITS DETECTED.

SAMPLE IMAGES PROCESSED VIA GCP COMPUTER VISION API - NO DIGITS DETECTED.

SAMPLE IMAGE PROCESSED VIA AWS REKOGNITION API - NO DIGITS DETECTED

SAMPLE IMAGE PROCESSED VIA AWS REKOGNITION API - SOME DIGITS DETECTED

FASTER-RCNN. OBJECT DETECTION APPROACH UTILIZED FOR IDENTIFYING DIGITS

HYPERPARAMETER SWEEPS USING WANDb

SAMPLE IMAGES WITH ANNOTATIONS

SAMPLE BASE AUGMENTATION OF IMAGES, TO IMPROVE THE TRAINING PROCESS

SPECIAL CASE 1: MODIFYING ANNOTATION FOR ONES - INCREASING THE SIZE OF THE BOUNDING BOX

SPECIAL CASE 2: HORIZONTAL FLIPPING CHANGES TWOS TO FIVES AND VICE VERSA

SPECIAL CASE 3: VERTICAL FLIPPING CHANGES NINES TO SIXES AND VICE VERSA

```
{'device': 'bp_monitor',
'hash-id': '20c5300672f84c10b4005ea0c1a08fe3',
'observations': {'obsv_0': '112', 'obsv_1': '76',
'obsv_2': '83'},
'predicted_boxes': [{'bounding_box':
[0.2510377466786194,
0.3077869415283203,
0.3547381758689880 4,
0.3852126598358154 3],
'text': '2'},
{'bounding_box': [0.2537219822406769,
0.4678944945335388,
0.3592096567153930 7,
0.5113921165466309],
'text': '1'},
{'bounding_box': [0.2558227181434631 3,
0.3901024162769317 6,
0.3557306528091430 7,
0.4312784075736999 5],
'text': '1'},
{'bounding_box': [0.3780727386474609 4,
0.3850133121013641 4,
0.4810033142566681,
0.4478096663951874],
'text': '7'},
{'bounding_box': [0.3773089349269867,
0.3044723272323608 4,
0.4840509295463562,
0.3781898319721222],
'text': '6'},
{'bounding_box': [0.4955586493015289 3,
0.2956322729587555,
0.573901891708374,
0.3468753695487976],
'text': '3'},
{'bounding_box': [0.4961883723735809 3,
0.3485622107982635 5,
0.5728340148925781,
0.4019385576248169],
'text': '8'}]}
```

JSON OUTPUT FROM ML ENGINE

FIG. 21B

COMPUTER-IMPLEMENTED SEGMENTED NUMERAL CHARACTER RECOGNITION AND READER

CROSS-REFERENCE TO RELATED APPLICATIONS

This application claims the benefit of priority to PCT Application No. PCT/US2022/081318, filed Dec. 9, 2022 (pending) and PCT Application No. PCT/US2022/074460, filed-Aug. 3, 2022 (pending), both of which claim priority to U.S. application Ser. No. 17/657,702 filed Apr. 1, 2022 (now U.S. Pat. No. 11,430,236), which claims the benefit of U.S. Provisional Appl. No. 63/287,731, filed Dec. 9, 2021, each of which is incorporated by reference in its entirety herein.

TECHNICAL FIELD

The field relates to digital health care and machine learning.

RELATED ART

Digital health care technology allows different health conditions to be measured or monitored. For example, a number of sensor devices detect blood glucose and blood pressure (BP) of individuals. Many devices use seven-segment displays. Seven segment displays are made up of three horizontal and four vertically oriented segments. These segments can be turned on or off to display any of the ten digits. Seven segment displays are inexpensive and easy to operate. Digital medical instruments like BP monitors and glucometers traditionally have a seven-segment display. Some newer sensor devices may have high-definition displays and may be Internet-enabled. But sensor devices with high-definition displays and Internet communication capability are unavailable or cost-prohibitive for many patients and health care providers.

Increasingly computer-implemented systems are being used to monitor and manage heath conditions of individuals. These systems are coupled to sensor devices to receive output data from the sensor devices representative of the health conditions being sensed. For example, these systems may be coupled to glucometers and BP monitors. The systems receive output data from the glucometers and BP monitors indicative of the sensed health conditions. In this way, the systems enable health care practitioners to monitor and manage blood glucose and blood pressure of individuals and other conditions relating to the sensed data.

However these monitoring and management systems often require sensor devices to be physically coupled to the systems. They also require patients to be physically present at the same location as the sensor devices coupled to the system which prevents telemedicine and other remote digital health care delivery. Many individuals cannot afford or access computer-implemented systems which can receive sensor output data. Also many individuals cannot afford or access sensor devices with Internet capability that can remotely communicate with management systems. All of these problems are especially burdensome in telemedicine and remote health care delivery where individual or patients may be located in a variety of locations that only have access to sensor devices with seven-segment displays.

Prior research for identifying seven segment numbers and datasets is limited and unworkable in practice. The inventors found existing datasets mimic the MNIST datasets and are not available for a "real" environment. See, E Finnegan, M Villarroel, C Velardo, and L Tarassenko, "Automated method for detecting and reading seven-segment digits from images of blood glucose meters and blood pressure monitors," *Journal of medical engineering & technology,* 43(6): 341-355, 2019. However, the inventors recognized in practice, a patient may upload an image with various tilts and orientations. Back-lights and reflection on the LCD display can create artifacts that are difficult to distinguish using traditional computer vision or classifier-based approach. Existing research heavily depends on first requesting the user to identify the area of interest and then individually identifying the digits. See, Varun N Shenoy and Oliver O Aalami, "Utilizing smartphone-based machine learning in medical monitor data collection: seven segment digit recognition," in *AMIA Annual Symposium Proceedings*, volume 2017, page 1564, American Medical Informatics Association, 2017. This may be difficult for older patients. See, E Finnegan, M Villarroel, C Velardo, and L Tarassenko, "Automated method for detecting and reading seven-segment digits from images of blood glucose meters and blood pressure monitors," *Journal of medical engineering & technology,* 43(6):341-355, 2019 (Finnegan et al.).

Synthetic datasets are used to simulate seven segment displays and augmented with images taken from a single device (one each for a BP monitor and glucometer). Ghugardare et al. and Finnegan et al. follow the process of template matching for identifying the digits. See, Rakhi P Ghugardare, Sandip P Narote, P Mukherji, and Prathamesh M Kulkarni, "Optical character recognition system for seven segment display images of measuring instruments," *TENCON* 2009-2009 *IEEE Region* 10 *Conference*, pages 1-6, IEEE, 2009, and Finnegan et al. Kanagarathinam et. al have a dataset of only 169 images in COCO format. See, Karthick Kanagarathinam and Kavaskar Sekar, "Text detection and recognition in raw image dataset of seven segment digital energy meter display," *Energy Reports,* 5:842-852, 2019, Kulkarni et. al use a 7-step approach using pixel density feature extraction achieving a 79% accuracy. See, Prachi H Kulkarni and Pratik D Kute, "Optical numeral recognition algorithm for seven segment display," 2016 *Conference on Advances in Signal Processing* (CASP), pages 397-401, IEEE, 2016. Savlolainen et al. have a dataset of 7 mn images of clock displays. However, the authors could only find 7.46% of them are human-readable. See, Tuomas Savolainen, Daniel Keith Whiter, and Noora Partamies, "Automatic segmentation and classification of seven-segment display digits on auroral images," *Geoscientific Instrumentation, Methods and Data Systems,* 5(2):305-314, 2016. Finally, Varun et al. use a classification approach where the user needs to identify the area of the image to be cropped. See, Varun N Shenoy and Oliver O Aalami, "Utilizing smartphone-based machine learning in medical monitor data collection: seven segment digit recognition," *AMIA Annual Symposium Proceedings*, volume 2017, page 1564, American Medical Informatics Association, 2017.

A number of attempts at identifying numbers in seven-segment displays have been made and fall short. There is a significant difference in the methods used to identify the regions (region extraction) and digit classification. Finnegan et. al. uses a blob extraction and clustering technique, but it achieves very low accuracy in detecting & classification of digits—51.5% for glucometer readings and 47% for bp monitors. The low accuracy makes it infeasible for production deployment. Mariappan et al. and Ghosh et al. developed a GUI for patients to identify the region of interest (ROI) and then used a OCR system to identify the individual digits. See, Muralindran Mariappan, Vigneswaran Ramu, Thayabaren Ganesan, Brendan Khoo, and Kumarheshan Vellian, "Virtual medical instrument for otorob based on labview for acquiring multiple medical instrument lcd reading using optical character recognition," *Proceedings from the International Conference on Biomedical Engineering and Technology* (IPCBEE), volume 11, pages 70-74, 2011; and Soumyadip Ghosh and Suprosanna Shit, "A low cost data acquisition system from digital display instruments employing image processing technique," 2014 *International Conference on Advances in Computing, Communications and Informatics* (ICACCI), pages 1065-1068, IEEE, 2014. The methods discussed above are limited in their application all have been tested on a limited number of devices. This makes their production deployment problematic and unworkable for telemedicine or health care management systems.

What is needed are computer-implemented methods, systems and devices that enable sensor devices having seven segment displays to be used to sense health conditions of individuals and to provide data readings obtained by sensor devices having seven segment displays to remote management systems.

BRIEF SUMMARY

Computer-implemented methods, systems and computer-readable storage medium are provided for numeric character recognition of numerals shown in a segmented display on a sensor device.

In an embodiment, a computer-implemented method includes capturing a digital image of a segmented display of numeric values shown on a sensor device and sending the digital image to a remote health management system having a reader. Further steps may include storing the digital image in a computer-readably memory, and processing the digital image at the reader to determine a sensor reading representative of the numeric values in the segmented display of the sensor device.

In an aspect, the computer-implemented method may include processing having steps of analyzing the digital image using optical character recognition to determine a first array of data, analyzing the digital image using a trained machine learning (ML) model to determine a second array of data, and evaluating the first and second arrays of data to obtain the sensor reading representative of the numeric values in the segmented display of the sensor device.

In a further aspect, the evaluating may include comparing the first and second arrays of data to determine whether data in the first and second arrays is identical or empty, outputting an output array of data having data from the first or second array of data when identical and from the first or second array that is not empty, and otherwise arbitrating the first and second arrays of data according to test criteria to obtain an output array of data when the comparing determines the first and second arrays of data are not identical and empty.

In a still further aspect, the computer-implemented method may include temporarily saving the obtained output array of data in computer-readable memory along with an identifier associated with the digital image. Other steps may include displaying the sensor reading information as numeric values along with the associated digital image for confirmation, and enabling a user to edit or select the numeric values and submit an input indicative of user confirmation.

In an embodiment, the method may further include training an ML engine with a training dataset of images to obtain the trained ML model. The training dataset may include base images of different sensor reading devices having segmented numeral displays. The training may include steps of augmenting base images in the training dataset to generate a synthetic training dataset that includes base augmentations of each base image in the training dataset. The training may also include applying images in the training dataset to the ML engine, evaluating candidate models using objection detection, minimizing a loss function and tuning hyper-parameters to obtain the trained ML model.

In another embodiment, a computer-implemented system for numeric character recognition of numerals shown in a segmented display on a sensor device over a data network is provided. The system includes a computing device that captures a digital image of a segmented display of numeric values shown on a sensor device for output over the network, and a reader that processes the received digital image to determine a sensor reading representative of the numeric values in the segmented display of the sensor device.

In further embodiment, a computer-implemented platform is provided for numeric character recognition of numerals shown on segmented displays on sensor devices and captured in digital images by digital cameras in remote computing devices coupled to the platform over a data network. The platform may have an image manager and a reader. The image manager is configured to manage a plurality of digital images, each digital image being representative of a segmented display of one or more numeric values shown on a respective sensor device. The reader is configured to process a stored digital image to determine a sensor reading representative of the numeric values in the segmented display of the sensor device.

Further embodiments, features, and advantages of the invention, as well as the structure and operation of the various embodiments of the invention are described in detail below with reference to accompanying drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

Embodiments are described with reference to the accompanying drawings. In the drawings, like reference numbers may indicate identical or functionally similar elements. The drawing in which an element first appears is generally indicated by the left-most digit in the corresponding reference number.

FIG. 10 shows a sample image processed via an AWS Rekognition API.

FIG. 11 shows a sample image processed via a GCP Computer Vision API.

FIG. 12 shows a sample image in color processed via AWS Rekognition API with no digits detected.

FIG. 13 shows a sample image in color processed via AWS Rekognition API with some digits detected.

FIG. 14 is a diagram illustrating a Faster-RCCN used in a ML Engine according to an embodiment of the present invention.

FIG. 15 is a diagram illustrating hyperparameter sweeps according to an embodiment.

FIG. 16 shows sample images in color with annotations captured in a test according to an embodiment.

FIG. 17 shows sample images in color of base augmentation captured in a test according to an embodiment.

FIG. 18 shows exception cases with sample images in color modifying annotation for ones and increasing bounding box size in a test according to an embodiment.

FIG. 19 shows exception cases with sample images in color with horizontal flipping in a test according to an embodiment.

FIG. 20 shows exception cases with example images in color with vertical flipping in a test according to an embodiment.

FIG. 21B shows an output array of data obtained from a ML Engine corresponding to the input image of FIG. 21A according to an embodiment.

DETAILED DESCRIPTION

Embodiments of the present invention provide computer-implemented methods, systems and devices having segmented numeral character recognition. In embodiment, users may take digital pictures of a seven-segment display on a sensor device. For example, a user at a remote location may use a digital camera to capture a digital image of a seven-segment display on a sensor device. The digital camera may be a digital camera provided on a computing device, such as, a smartphone having data storage and communication capability. Captured images of a seven-segment display of the sensor device may then be sent or uploaded over a network to a remote health platform. The health care management platform includes a reader that processes the received images to determine sensor readings representative of the values output on the seven-segment displays of the remote sensor devices. Machine learning is used to identify numeric characters in images associated with seven-segment displays. In this way, a remote heath management system can obtain sensor readings from remote locations when users only have access to sensor devices with seven-segment displays.

Embodiments refer to illustrations described herein with reference to particular applications. It should be understood that the invention is not limited to the embodiments. Those skilled in the art with access to the teachings provided herein will recognize additional modifications, applications, and embodiments within the scope thereof and additional fields in which the embodiments would be of significant utility.

In the detailed description of embodiments herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The inventors provide further description below with respect to an example implementation and advantages not intended to be limiting.

System

Figure 1:
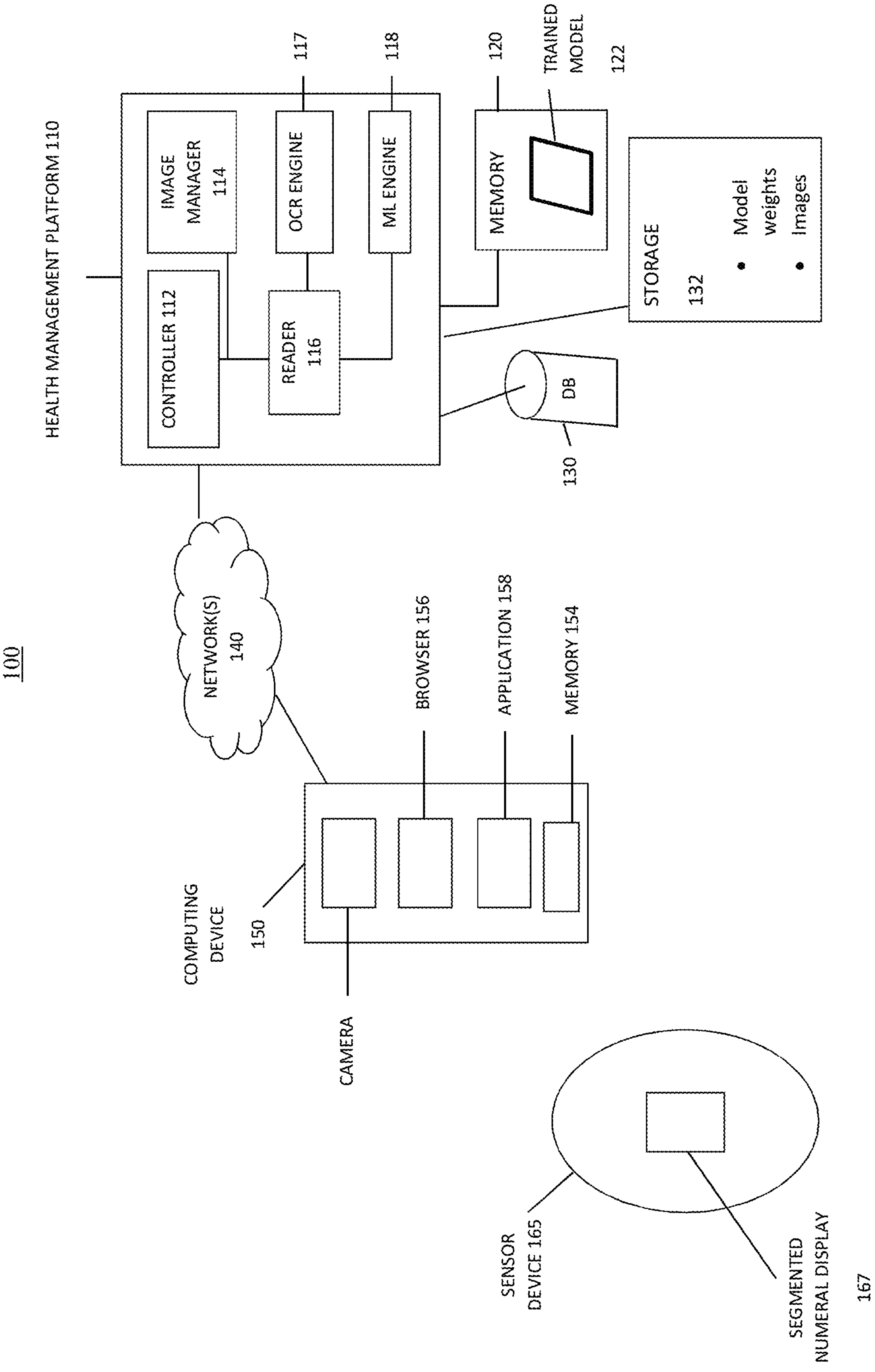
FIG. 1 is a diagram of an online system for segmented numeric character recognition according to an embodiment of the present invention.

FIG. 1 is a diagram of an online system 100 for segmented numeric character recognition according to an embodiment. System 100 includes an online health management platform 110. Health management platform 110 is coupled to computer-readable memory 120 and database 130: One or more computing devices 150 are coupled over one or more data networks 140 to health management platform 130. A user may access health management platform 110 through computing device 150.

System 100 is configured to receive digital images of segmented numeral displays. For example, sensor device 165 has a segmented numeral display 167. A user may use computing device 150 to capture a digital image of one or more segmented numerals shown on display 167. In one embodiment, computing device 150 includes camera 152, memory 154, browser 156, and application 158. One or more processors and a display may also be included in computing device 110. Camera 112 may be a digital camera that captures a digital image of segmented numerals on display 167 and stores the digital image in memory 154. Browser 156 or application 158 may be used to output the captured image to health management platform 110. Health management platform 110 may receive and process the image to recognize segmented numeral characters in the captured image.

In one embodiment, health management platform 110 includes controller 112 coupled to image manager 114 and reader 116. Reader 116 is coupled to optical character recognition (OCR) engine 117 and a trained machine learning (ML) engine 118. Controller 112 controls the initiation and sequence of operation of components in health management platform 110 including image manager 114 and reader 116. Image manager 114 manages the storage and access to images. This can include the storage and access of data and images in memory 120 and in database 130. Reader 116 accesses and processes a captured image.

Reader 116 uses OCR Engine 117 and ML Engine 118 to process data in the captured image. OCR engine 117 may be any type of optical character recognition engine. OCR engine 117 uses OCR to analyze the intensities of pixel data in an image and identify characters, such, as numerals. The accuracy and ability of an OCR algorithm then depends upon image quality. Poor quality images may lead to poor, uncertain and even missing numeric recognition results by an OCR engine. Current OCR technology also has shown inconsistent results with seven segment displays. ML engine 118 may be any type of ML engine trained to detect numeric characters used a trained ML model 122. For example, prior to operation, a ML engine 118 may be trained on a training dataset to obtain trained ML model 122. In particular, ML engine 118 may test a number of candidate models using machine learning to obtain a final trained ML model. The training may involve processing sets of base and augmented images through a deep neural network layer with object detection (such as Faster R-CNN). This is done over multiple sets of the data such that the loss function is minimized. Parameters of the model are tuned (known as hyper-parameter tuning) until a final model is selected from candidate models. The trained ML model 122 is then used by ML engine 118 during operation to classify an image and recognize numeric characters as described herein. In this way, the quality and accuracy of numeric recognition can depend on the quality of a training dataset and type of neural network and other machine learning techniques used. Machine learning engine operation and training thereof for ML Engine 118 and trained ML model 122 is described in further detail below and with respect to an example implantation and test results, intended to be illustrative and not limiting.

Reader 116 evaluates output data from both engines 117, 118 to determine values for segmented numerals. Reader 116 then outputs values corresponding to sensor reading information for storage in database 130. By arbitrating outputs of both OCR engine 117 and ML engine 118, reader 116 can recognize numerals in images of segmented displays more accurately and reliably even in telemedicine applications having remote sensor devices with relatively low-resolution displays, poor lighting, a variety of types of sensor devices, or operated by users with little or no training in sensor reading.

Health management platform 110 can be any type of online platform including, but not limited to, a Software as a Service (SaaS) or other platform. In one example, not intended to be limiting, health management platform 110 may be part of or coupled to the GUARDIAN platform available from RediMD, LLC. In one embodiment, health management platform 110 including its components (controller 112, image manager 114, reader 116, OCR engine 117, ML engine 118) may be implemented on one or more servers at the same or different locations and may be implemented using one or more application programming interfaces (APIs) as needed to access different services to perform operations as described herein. Health management platform 110 may be coupled to one or more web servers supporting World Wide Web services, communication protocols or standards.

Database 130 may be one or more databases, such as, a relational database used with a database management system. A storage device 132 may be coupled to platform 110. Storage device 132 can store model weights for use in training ML engine 118 and images or other data needed by platform 110. In one example, storage device 132 may be a disk storage device.

Network 140 can be any type of network including, but not limited to, a local area network, medium area network, or the internet. Network 140 can be a data or telephony network or any combination thereof.

Computing device 150 can be any type of computing device including, but not limited to, a smartphone, laptop, desktop, tablet, workstation, or other computing device having at least one processor and a computable readable memory 154. Browser 156 may be any type of browser including, but not limited to, a SAFARI browser from Apple Inc., CHROME browser from Google LLC or EDGE browser from Microsoft Inc. Application 158 may be a standalone application or may operate as a web application with browser 156. For example, application 158 may be downloaded by a user from an application store or other site. Similarly, a web application with browser 156 may be accessed by directing the browser to a portal page or other entry page allowing a user to access health management platform 110. For clarity, the term online application is used to refer to either application 158 or a web application supported by browser 156. Computing device 150 may further have an operating system as would be apparent to a person skilled in the art given this description.

Sensor device 165 may be any type of sensor device having a segmented numeral display, such as, a blood pressure device, glucose meter or other health sensor device. Segmented numeral display 167 may be any type of display configured to display one or more segmented numerals. A segmented numeral is a numeral represented in one to seven segments.

In one embodiment, health management platform 110 is coupled to computing device 150. Health management platform 110 outputs data in an online application operating between computing device 150 and health management platform 110. The online application may be an application inputting and outputting through browser 156 or may be a standalone application 158 running on device 150.

The operation of system 100 is described further below with respect to computer-methods and example user-interface (UI) pages shown in FIGS. 2-9.

Operation

Figure 2:
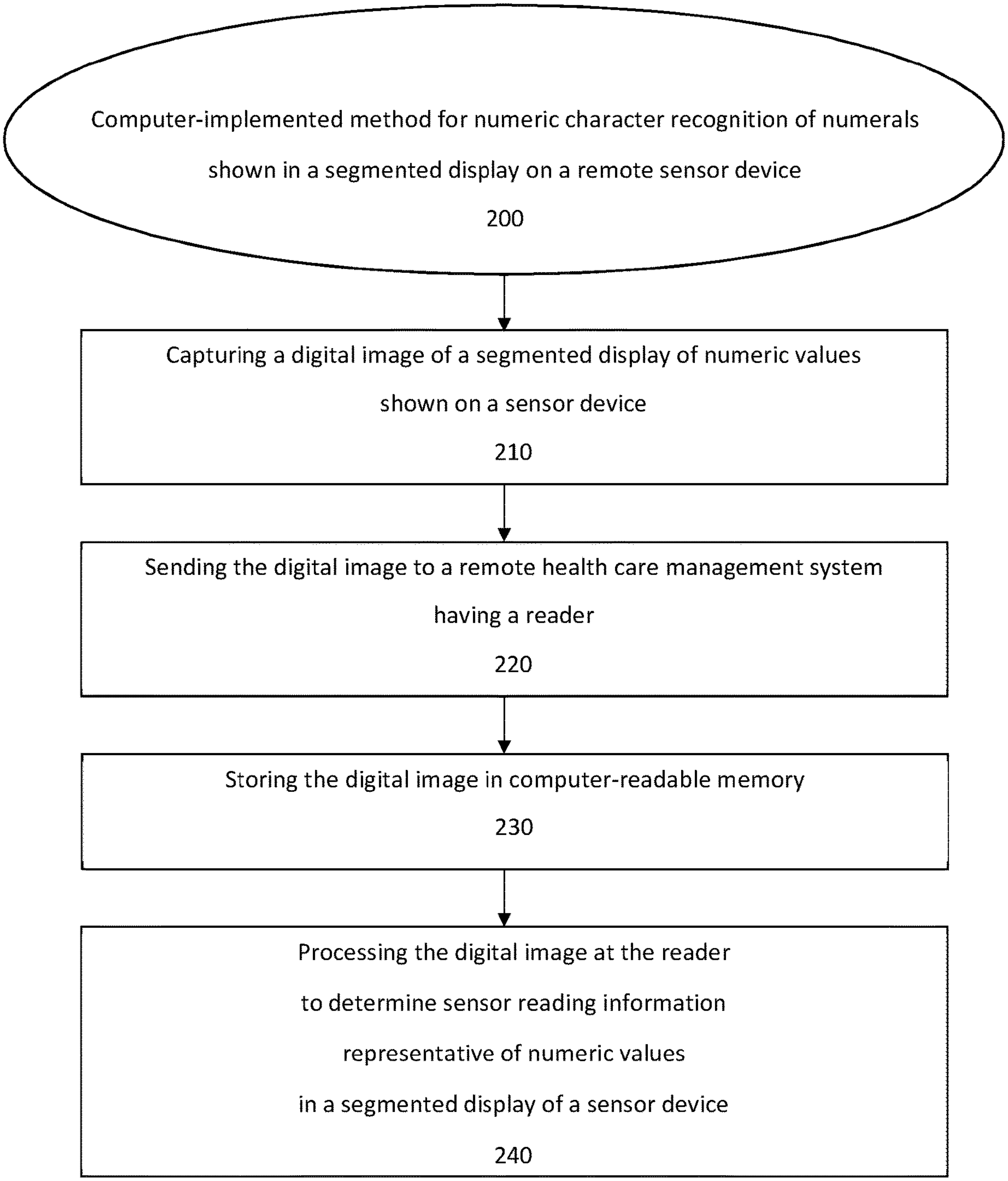
FIG. 2 is a flowchart diagram of a computer-implemented method for numeric character recognition of numerals shown in a segmented display on a remote device according an embodiment.

FIG. 2 is flowchart diagram of computer-implemented method 200 for numeric character recognition (steps 210-240). In step 210, a digital image of a segmented display of numeric values is captured. Computing device 150 having a camera 152 may be used to capture an image of a segmented numeral display 167. For example, computing device 150 may be a smartphone used by a user to take a picture of the segmented numeral display 167.

In step 220, the captured digital image of a segmented numeral display is sent to remote health management platform 110. A user may use browser 156 (or application 158) to upload and send the digital image to health management platform 110. In one embodiment, an online application may be used to facilitate uploading and sending of captured images to health management platform 110. For example, health management platform 110 may output one or more pages to enable a user to upload and send one or more images of segmented numerals shown on displays on a glucose sensor device or blood pressure sensor device as described further below with respect to FIGS. 5-7.

In step 230, the received image is stored in computable readable memory. For example, image manager 114 may receive an image corresponding to a registered user on health management platform 110 and store the image in memory 120, storage device 132 or database 130. For example, the received image may be stored in a record in database 130 or temporarily stored in memory 120 or more permanently stored in storage device 132.

In step 240, a digital image is processed to determine sensor reading information. The sensor reading information is representative of the numeric values in the segmented display of a sensor device. For example, reader 116 may retrieve a stored digital image from memory 120, storage device 132 or database 130. Reader 136 then processes the digital image to determine sensor reading information representative of the numeric values. Both OCR engine 117 and ML engine 118 are used to recognize numeric characters from a segmented numeral display image. Reader 116 arbitrates between the outputs OCR engine 117 and ML engine 118 to determine sensor reading information which includes the numeric values. The determined sensor reading information may then be stored in memory 120, storage device 132 or database 130. In one example, sensor reading information is first displayed to a user along with the image for comparison and confirmation. For example, health management platform 110 may output one or more pages to enable a user to compare and confirm determined sensor reading information with captured images of segmented numerals shown on displays on a glucose sensor device or blood pressure sensor device as described further below with respect to FIG. 8.

After a positive confirmation, the sensor reading information may be stored in a record in database 130 for subsequent use or access by health management platform 110. If confirmation is not positive, the sensor reading information may be flagged for administrative review. Processing of the digital image in step 240 according to one embodiment is described further below with respect to FIG. 3 (steps 310-350).

Digital Image Processing

Figure 3:
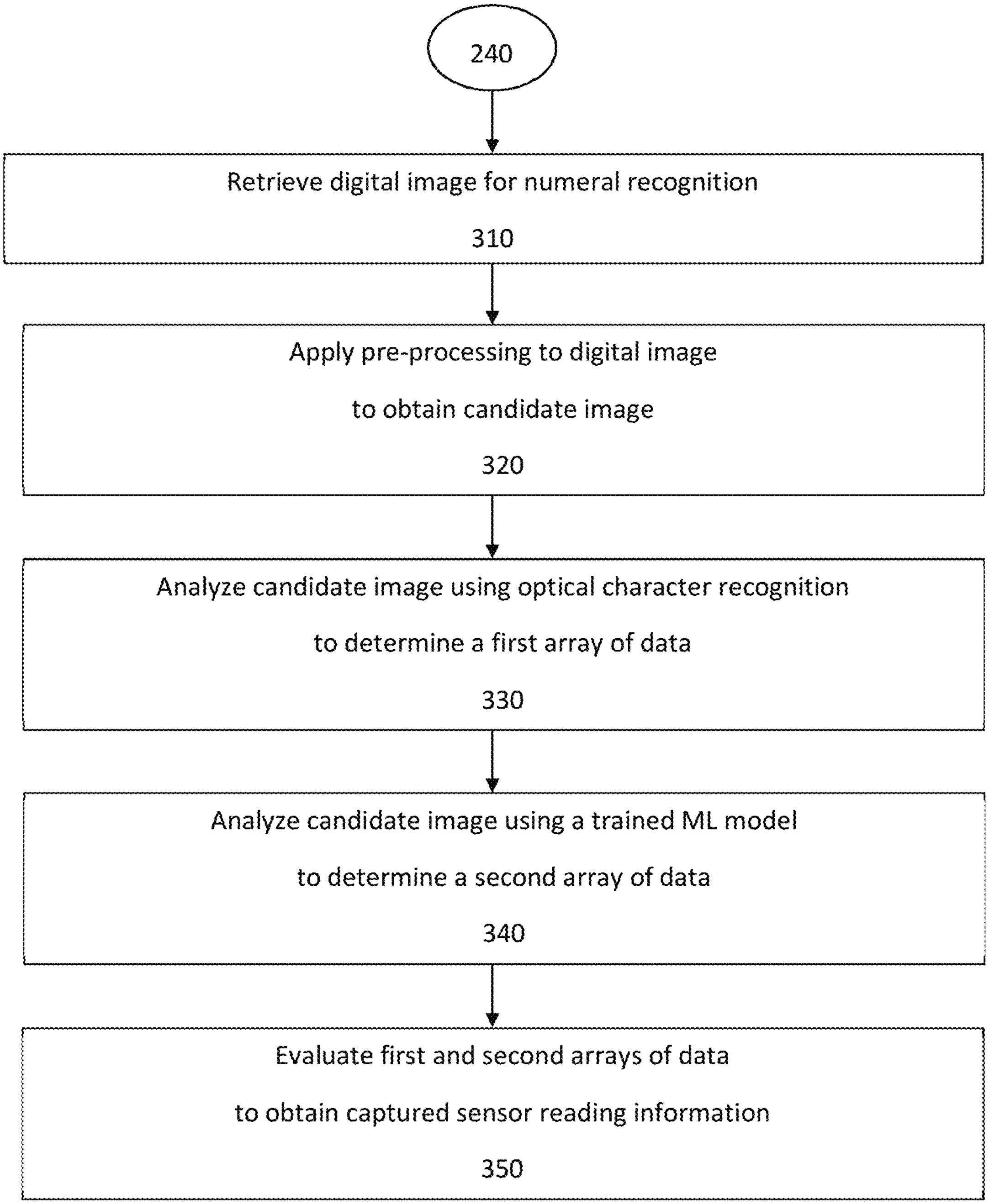
FIG. 3 is a flowchart diagram showing the digital image processing step of FIG. 2 in an embodiment.
Figure 17:
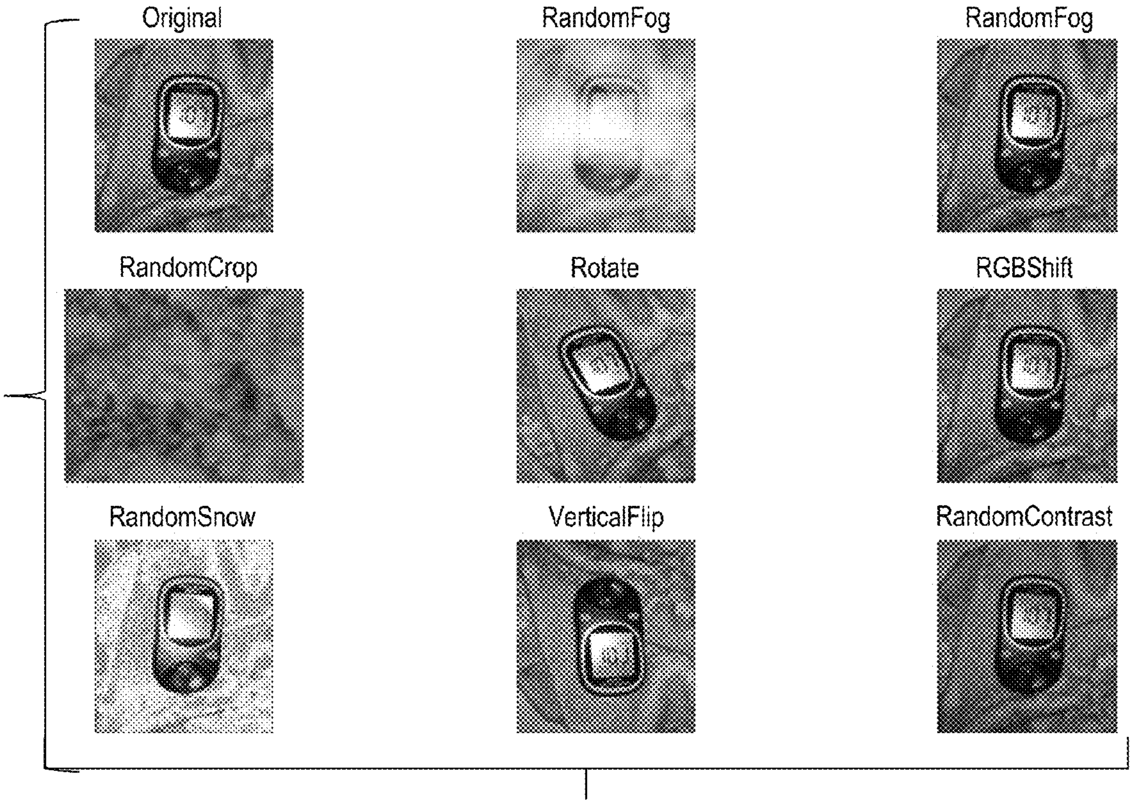

As shown in FIG. 3, in step 310 a digital image is retrieved for numeral recognition. For example, reader 116 may retrieve a digital image from memory 120, storage device 132, or database 130:

In step 320, preprocessing is applied to a digital image to obtain a candidate image. For example, reader 116 (or image manager 114) may preprocess pixel data and metadata (such as size or orientation data) in the image to facilitate further image analysis. This preprocessing may include detecting if exif orientation data for an image exists and if so, rotating the image so that the image is top up in a landscape orientation. Preprocessing may also include resizing the image to a 300 pixel wide size or other predetermined size. Finally, preprocessing may include converting the image to grayscale to facilitate OCR processing. These pre-processing examples are illustrative and other known pre-processing techniques may be used to obtain a candidate image better suited for further numeric character recognition processing. The image may also be augmented for better response from the ML engine. Sample base augmentations are shown in FIG. 17.

In step 330, the candidate image obtained after preprocessing in step 320 is analyzed using optical character recognition to determine a first array of data. For example, reader 116 may pass the preprocessed candidate image to OCR Engine 117. OCR Engine 117 may execute an OCR algorithm to determine a first array of data. For example, OCR Engine 117 may be an Amazon Rekognition OCR service (or similar services) that returns a JSON serialized formatted object containing bounding rectangles, relative x,y positions, height, width and confidence score of both lines and texts and individual words. This returned object and information therein can be used to create a first array of data returned in step 330.

In step 340, the candidate image obtained after the preprocessing in step 320 is also analyzed using a trained Machine Learning model to determine a second array of data. For example, reader 116 may pass the candidate image to ML Engine 118. ML Engine 118 uses a trained model 122 to detect the digits and identify the readings on the uploaded images. In one implementation, the output of the ML Engine 118 is a json file with bounding boxes, the identified digits therein, confidence of identification and other inferred data. ML engine 118 then outputs a second array having data representative of the classifier results.

Figure 21A:
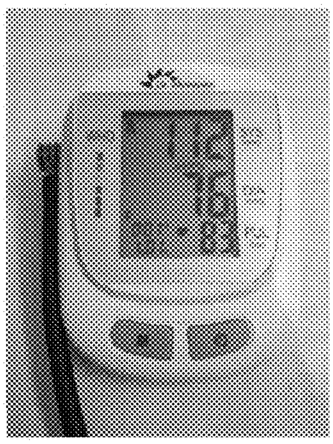
FIG. 21A shows an example input image in color.

In one embodiment, ML Engine 118 may be an inference engine hosted on Amazon Web Services as a lambda process using a RESTapi interface. Reader 116 passes the candidate image to the AWS Lambda function that executes Detectron2Go (D2Go) inference engine library released by Facebook AI under the Apache 2.0 license. Detectron2Go loads the r-cnn Seven Segment trained model 122 to identify and classify digits in the image and output results. The results may contain bounding boxes size, location, confidence score and classifications created by the inference engine. The returned results can be used to create a second array of data returned in step 340. For example, ML Engine 118 may output results to reader 116. Based on the results, reader 116 may generate a second array of data which includes bounding boxes, size, location, confidence scores and classifications created by the inference engine. For example, FIG. 21B shows output from ML engine 118 in a JSON file with identifying information for device, a hash ID for an associated input image shown in FIG. 21A, observations data (numerals 112, 76, 83), and predicted boundary boxes and text for seven digits (2,1,1,7,6,3,8).

In step 350, the determined first and second arrays of data are then evaluated to obtain captured sensor reading information. For example, reader 116 may evaluate the first and second arrays of data obtained in steps 330 and 340 and determine a final sensor reading information. This final sensor reading information represents the numeric values shown in the segmented display 167 of sensor device 165.

Figure 4A:
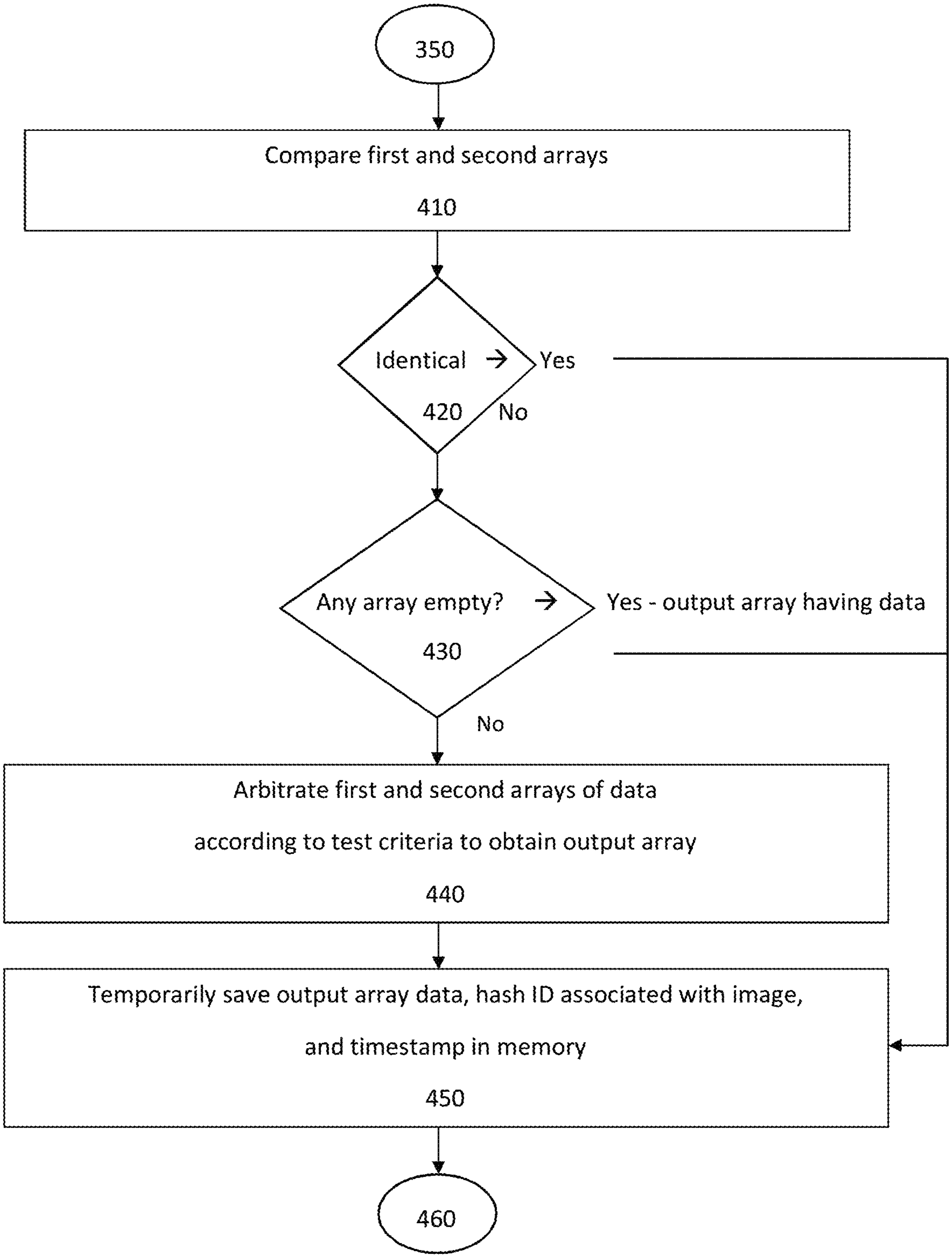
FIGS. 4A and 4B are flowchart diagrams showing in further detail the evaluation of array data to obtain sensor reading information step of FIG. 3 in an embodiment.
Figure 4B:
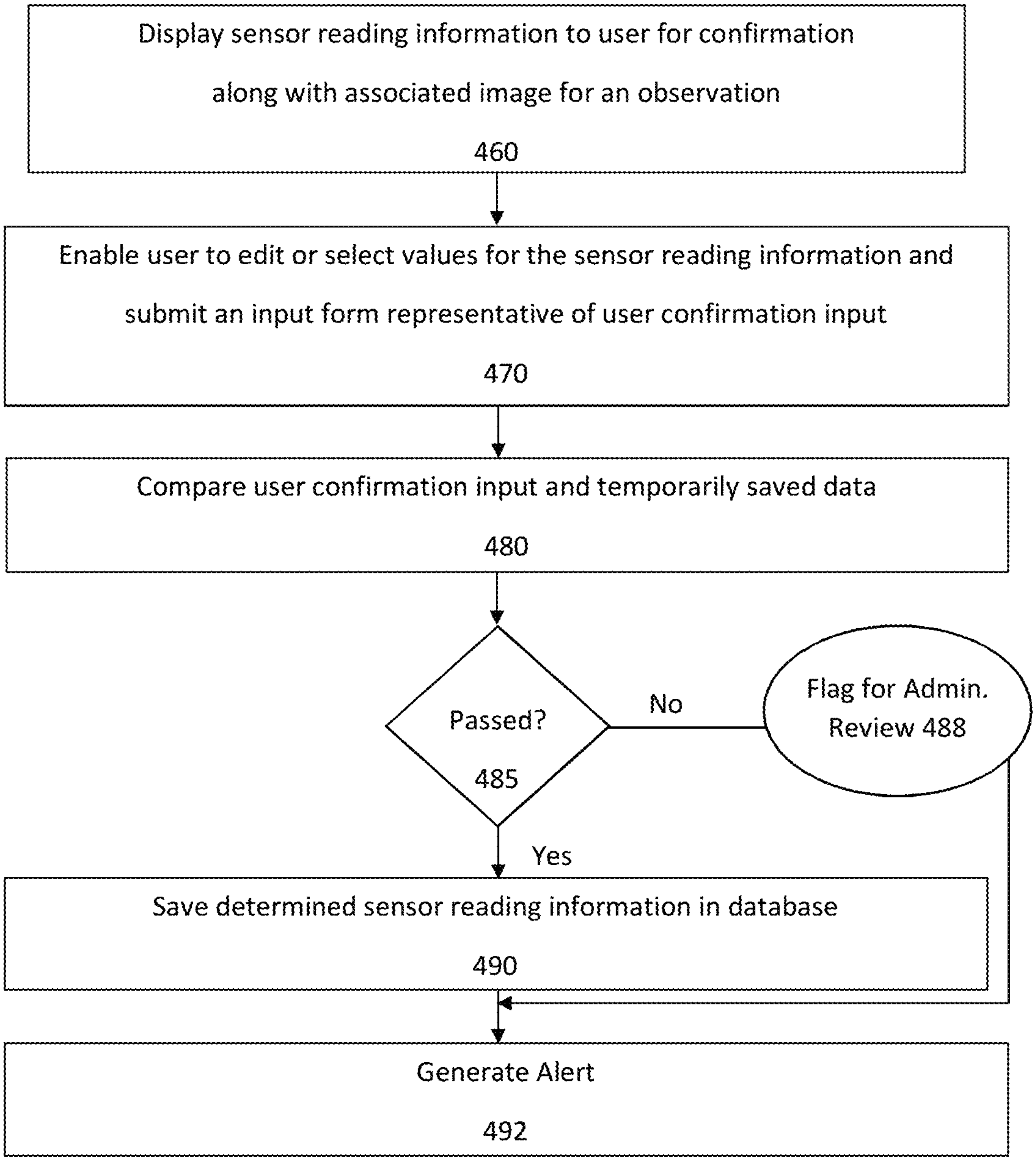

The operation of step 350 is described in further detail with respect to an embodiment of FIGS. 4A-4B (steps 410-492). In one embodiment, steps 410-492 are carried out by reader 116.

Consider the following examples of evaluating images relating to a glucose sensor device (glucometer) and blood pressure sensor device and associated criteria that may be used in reader 116. Reader 116 can process glucometer and blood pressure images differently to detect numerals. A glucometer often provides one significant data point, the glucose level in mg/dL. A blood pressure device often returns three significant data points; systolic pressure and diastolic pressure in inHg and pulse as BPM. Accordingly, the value of the largest word, closest to the top of the image, is captured by reader 116 for blood sugar monitoring. Blood pressure requires the value of the three largest words in the image. The values are placed by reader 116 in descending order of size and secondarily, location relative to the top of the image.

In this way, the resulting word values obtained by OCR engine 117 for recognized characters are sorted by size and relative position and returned in a first array. ML engine 118 returns bounding boxes and classifications that contain information about individual digits in the image. These individual digits are joined together logically based upon relative position to each other to create multi-digit numbers or observations within larger bounding boxes. The number values or observations created by joining digits are arranged by size and relative position just like or similar to the OCR results and returned in a second array. The sensor image may contain other extraneous information like date and time information and other meta data provided by the sensor. ML engine 118 may ignore this information while processing only the relevant sensor data (see sample images provided in FIG. 16 and FIG. 21A).

Reader 116 receives the first and second arrays returned from both OCR engine 117 and ML engine 118 (steps 330, 340 above). For example, these arrays may be returned to reader 116 as a result of OCR and AI/ML API calls to services performing OCR and applying machine learning (inference) with a trained model as described herein. Each array may contain values or may be empty. The OCR results are usually correct or missing. The OCR rarely returns incorrect values. The ML engine almost always returns values but may contain values that have low confidence levels.

In step 410 as shown in FIG. 4A, the first and second arrays of data are compared. If the first and second arrays of data are identical (decision step 420), then control proceeds to step 450 for temporary storage. Identical arrays are the best case scenario and either array may be used to populate an input form for user confirmation. If the first and second arrays of data are not identical, control proceeds to step 430. In step 430, reader 116 evaluates whether any of the first and second arrays of data are empty. If yes, control proceeds to output the first or second array having data (that is not empty) and then control proceeds to step 450. The empty array may be discarded. If both first and second arrays of data are not empty, then control proceeds to step 440.

In step 440, first and second arrays of data are arbitrated according to test criteria to obtain an output array of data. For example, reader 116 may arbitrate between the data in the first and second arrays according to test criteria to select optimal data for including in the output array. For example, the test criteria may be a reasonable test. Reader 116 may apply reasonable tests on the data in both the first and second arrays. Missing values, extraneous values and values outside of reasonable assumptions are discarded. If conflicts remain after the reasonable test, then values having the highest confidence score are used to populate the output array. The output array has an initial obtained sensor reading information for recognized numerals.

In step 450, the output array of data having the sensor reading information is temporarily saved. For example, the output array data may be saved in memory 120 by reader 116. In step 450, reader 116 may also temporarily save a hash ID associated with the image and an associated timestamp in memory along with the output array data. Control then proceeds to step 460. A hash ID for example may be a unique identifier of the image such as hash, fingerprint, or other function generated to uniquely identify the associated image. A timestamp may be a dat4 and time in which the image was captured by the digital camera.

As shown in FIG. 4B, in step 460, the initial sensor reading information is displayed to a user for further confirmation. The initial sensor reading information may be displayed along with an associated image for observation by the user at a display on computing device 150. In this way, the user can view the captured image of the segmented numeral display along with the values of the initial sensor reading information displayed to confirm that the sensor reading information is correct.

In step 470, a user is enabled to edit or select values for the sensor reading information and submit an input (such as a UI input form selection) representative of user confirmation. For example, a user may view a page on computing device 150 and his or her selection with respect to a confirmation is sent as a signal over network 140 to remote health management platform 110. (Alternatively, this comparison and confirmation may be performed by staff or other authorized users of health management platform 110 to reduce work of users.)

In step 480, user confirmation input is compared with the initial sensor reading information stored in temporarily saved data. If the comparison results in a pass (decision step 485), then control proceeds to step 490. If the comparison of the user confirmation input and temporarily saved data does not pass, then control proceeds to step 488 to flag the temporarily saved data for administrative review. This may include flagging a record associated with the captured image of a user with an administrative review flag.

In step 490, after the pass check in step 485, the determined initial sensor reading information is then stored in a record in database 130. In this way, database 130 may store the determined sensor reading information along with the captured image for a user. Control then proceeds to step 492 to generate one or more alerts.

Alerts may be output representative of one or more alert conditions detected throughout the processing of the captured image. Example alert conditions include but are not limited to:

- File not found (missing, insufficient permissions, disk error, corrupted file data)
- Invalid file type (Only .JPG, .PNG, .BMP files allowed)
- Malformed json load sent to ML engine
- No image data sent to ML engine
- Error while predicting from uploaded image data
- Error while post-processing of array data
- Upload failure (network connection failed)
- No data found (both arrays returned null values)
- Values out of range (Values entered in input fields exceed defined ranges)
- Update failed (Database update failed—multiple possibilities)
- No server response (API timed out or didn't connect)
- Server error (AWS/Lambda specific error message)
- Observation saved (transaction completed successfully)
- File successfully processed (image was processed and at least one of the arrays contained reasonable data).

Platform User-Interface

FIGS. 5-9 show example pages that may be displayed to one or more users coupled to a health management platform 130. For example, browser 156 may display one or more pages having data output by health management platform 110. Health management platform 110 may also receive data input by a user through browser 156.

Figure 5:
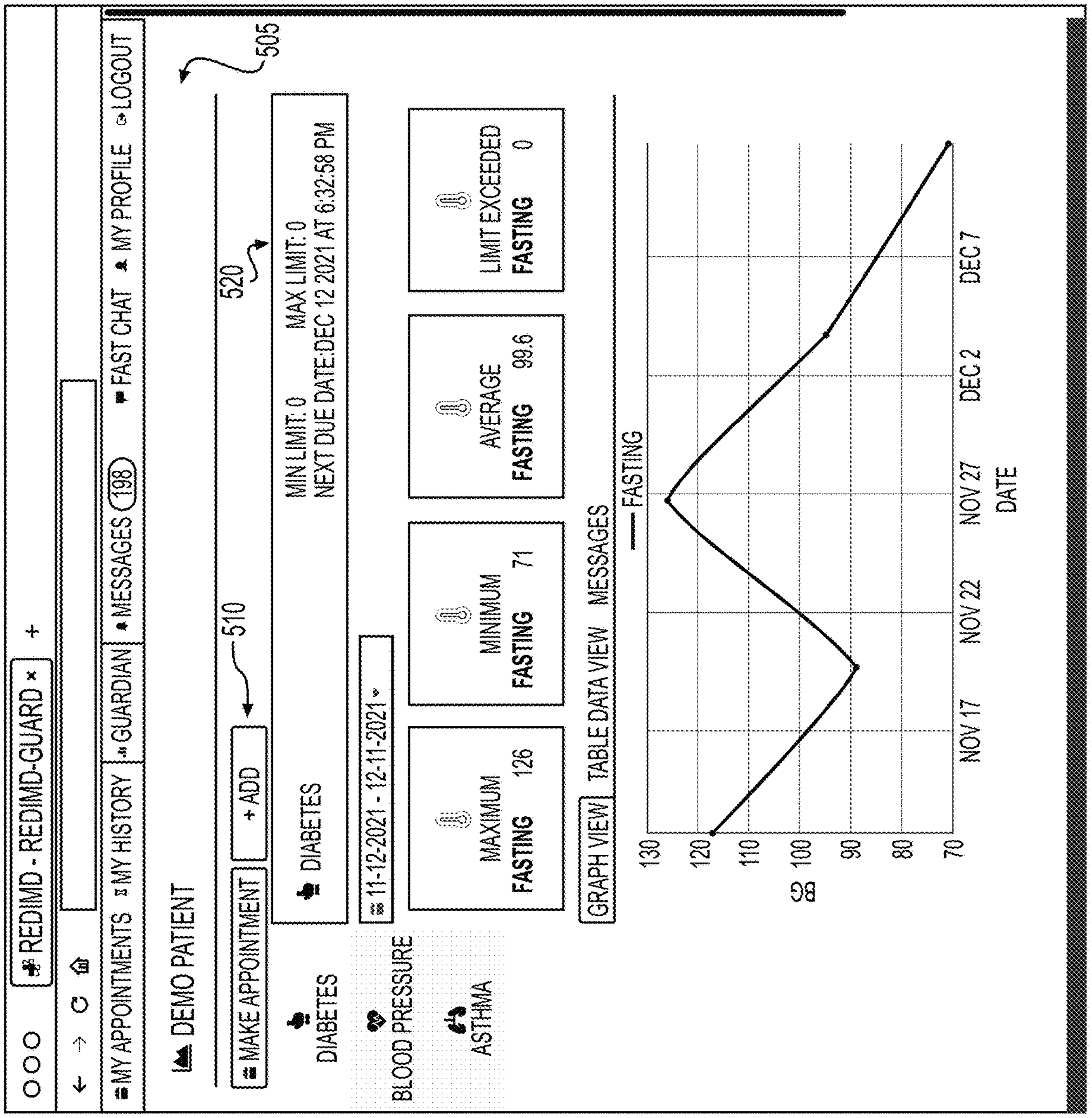
FIGS. 5-9 are diagrams of example pages that may be output for display to users according to an embodiment.

FIG. 5 shows an example main page that may be displayed to a user accessing health management platform 110. As shown on FIG. 5, page 500 (such as a browser tab) may be displayed. Page 500 includes a panel 505. Panel 505 may also include an add button 510 and a display area 520. Add button 510 enables a user to select to add a captured image of a segmented numeral display 167. Display area 520 may display information relating to healthcare management. For example, as shown on FIG. 5, display area 520 may include information relating to diabetes or other health conditions.

Figure 6:
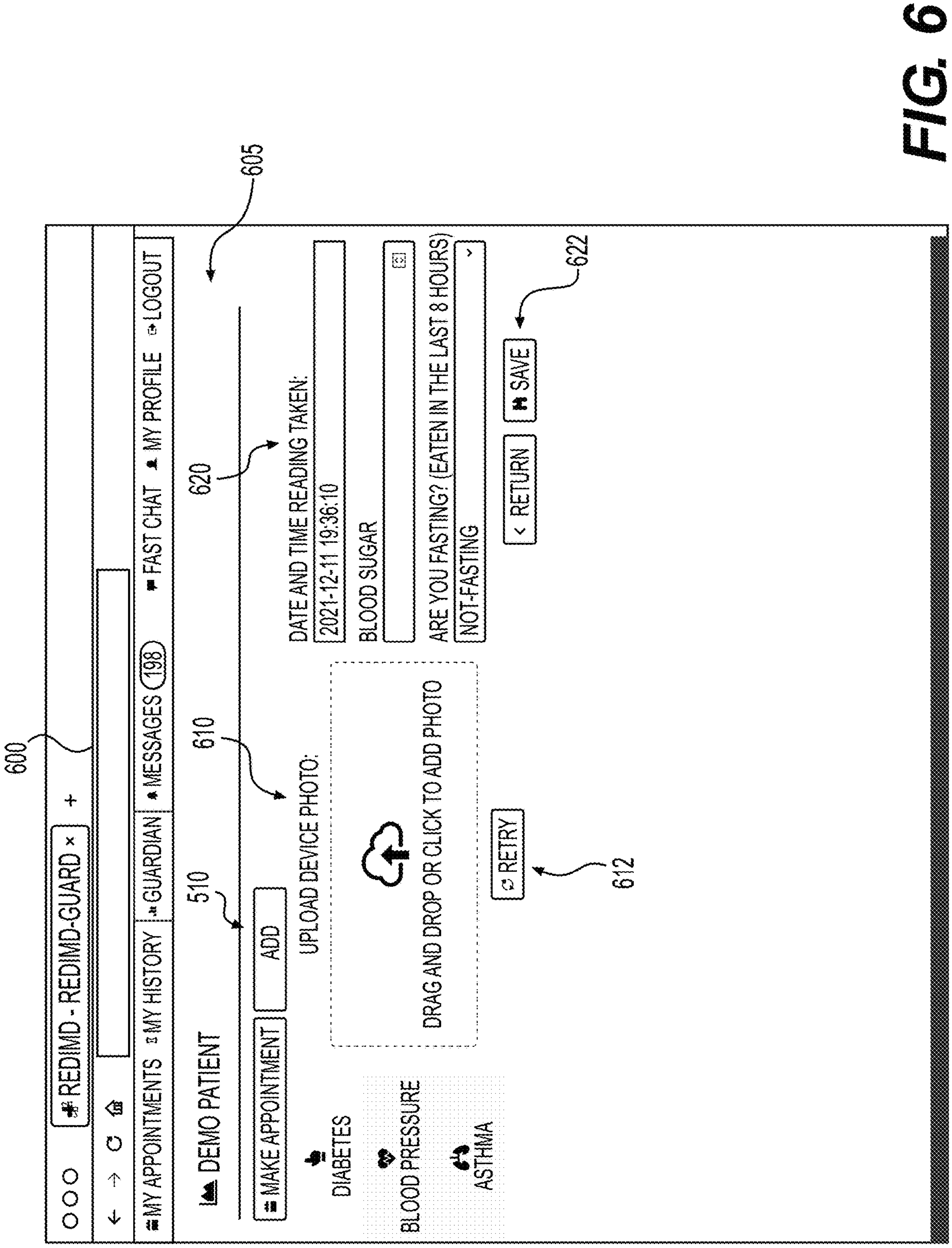

FIG. 6 shows a page 600 after add button 510 has been selected. Page 600 has a display area 605 including an upload device photo user interface (UI) element 610 and sensor reading confirmation UI element 620. Upload device photo UI element 610 enables the user to drag and drop or add a captured photo image. Panel area 605 may also include a button 612 that enables a user to select retry if an initial upload is unsuccessful.

Sensor reading confirmation UI element 620 includes one or more user interface elements for displaying sensor reading information and/or enabling a user to add, edit or delete the sensor reading information. This may include a text box, drop down menu, dial, or other user interface element. Buttons 622 may be provided below or near element 620 to enable a user to return control to a different page or to save the sensor reading information input. In the example of FIG. 6, sensor reading confirmation UI element 620 is configured for glucose sensor reading information. This includes a first box area to show, edit or enter date and time reading taken information and a second box area to show, edit or enter blood sugar reading values (e.g., a numeric value). A third box area enables a user to enter or edit fasting information (such as, not fasting within last eight hours). Editing as used herein may include adding, modifying or deleting.

Figure 7:
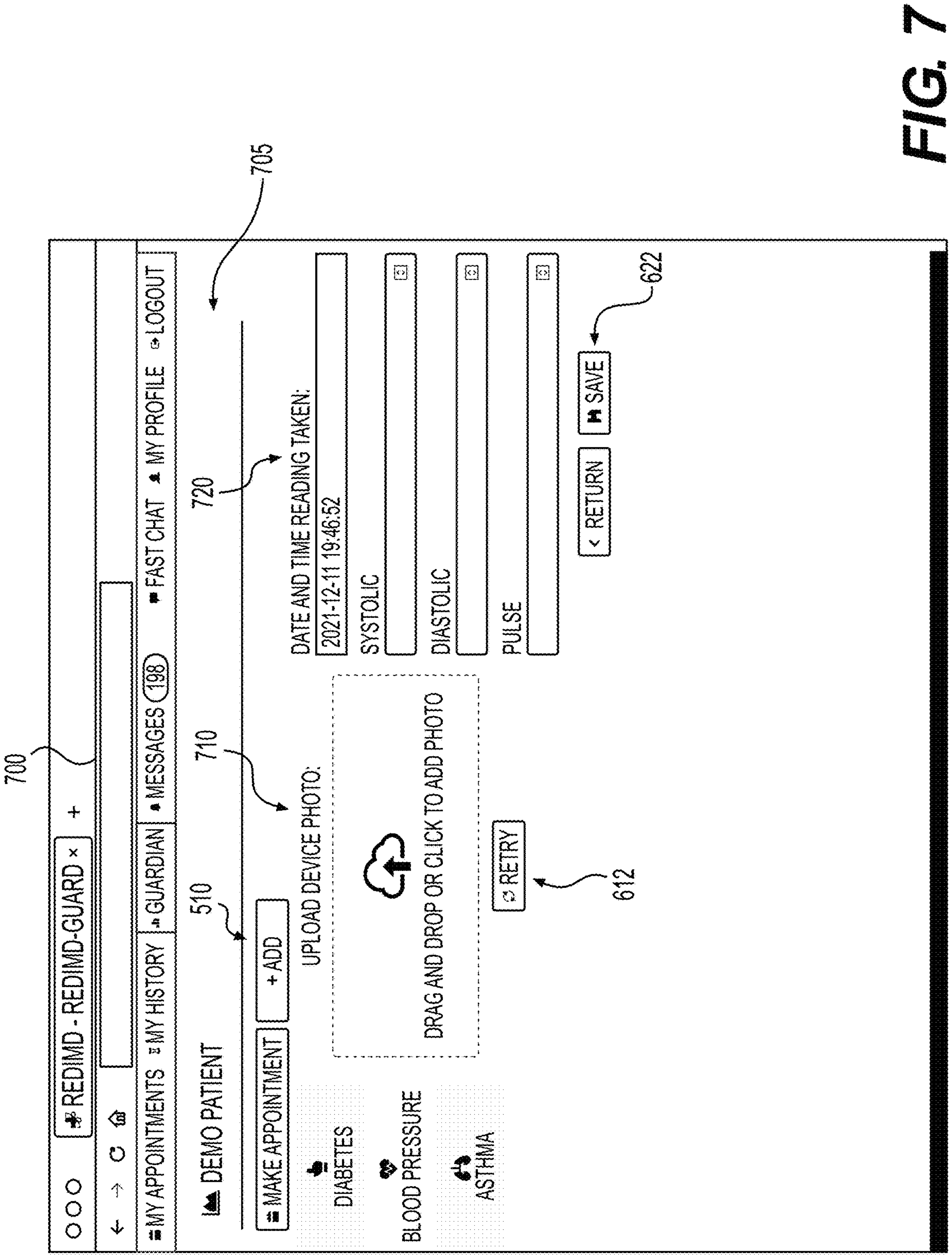

FIG. 7 shows a page 700 having an alternate input form configured for blood pressure reading information. Page 700 includes a panel 705 having an upload device photo UI element 710 and a sensor reading confirmation UI element 720. Upload device photo UI element 710 allow a user to upload an image of a blood pressure sensor display similar to UI element 610 described above for a glucose sensor display. UI element 720 includes information for adding blood pressure related sensor information. This can include systolic, diastolic or other types of blood pressure information. For example, UI element 720 may include a first box area to show, edit or enter date and time reading taken information. Second, third and fourth box areas are configured respectively to show, edit or enter numeric sensor reading values for blood pressure (systolic, diastolic) and pulse.

Figure 8:
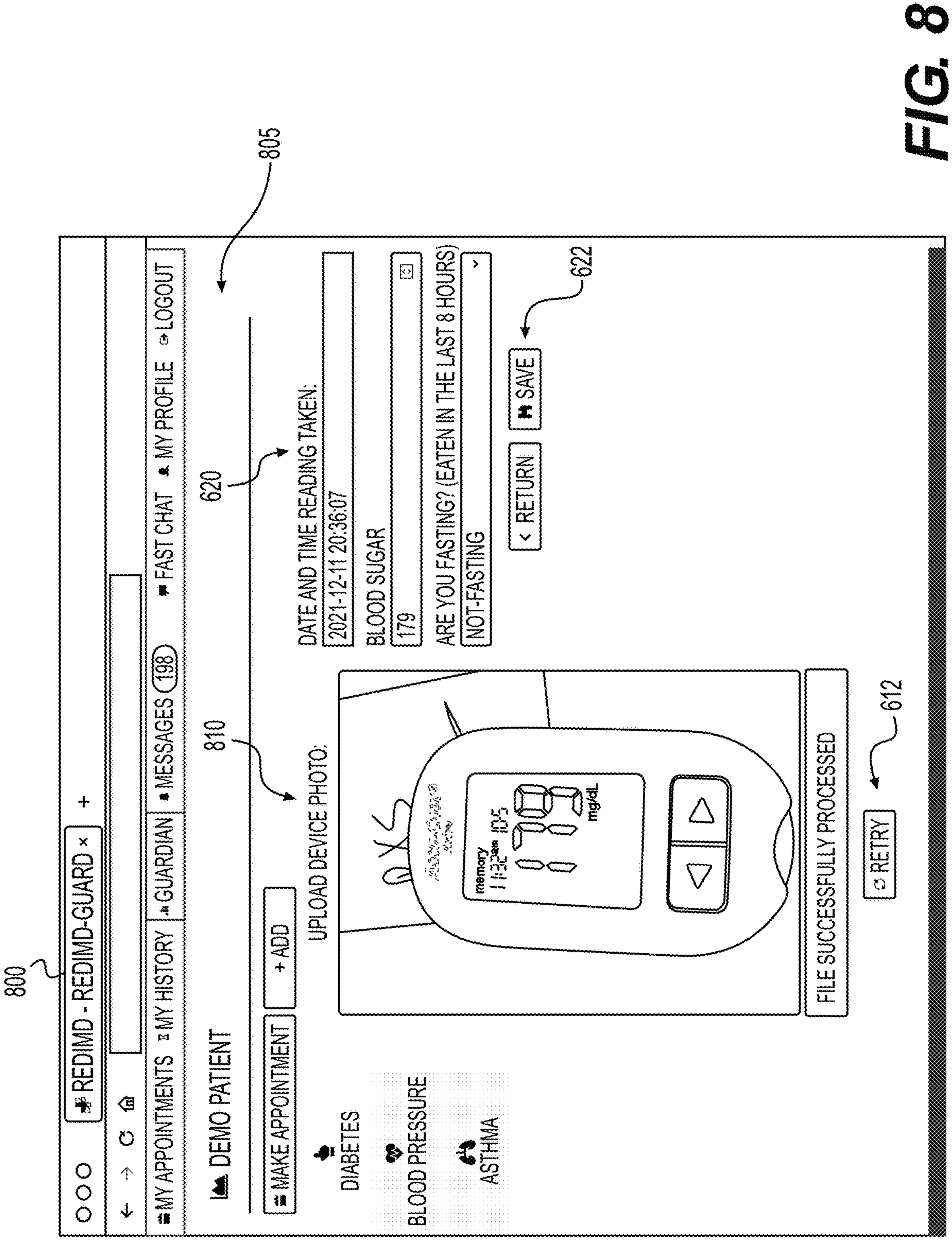

FIG. 8 shows a page 800 that may be displayed in response to an uploaded image photo. For example as shown in FIG. 8, a panel 805 may include a display area 810. Display area 810 shows an image of the uploaded captured image. This captured image may be a digital image of the segmented numeral display 167 captured by camera 152. Alongside the captured image area 810 is the sensor reading confirmation UI element 620. In this way, a user can compare side by side the captured image having the segmented numeral display and confirm that the determined segmented numeral display shown in UI element 620 matches. The user can further make edits into UI element 620 to correct and confirm the sensor reading information. When the user has confirmed the sensor information is correctly shown UI element 620, the user may hit save button 622. In this way, the confirmed sensor information may then be stored in health management platform 110.

Figure 9:
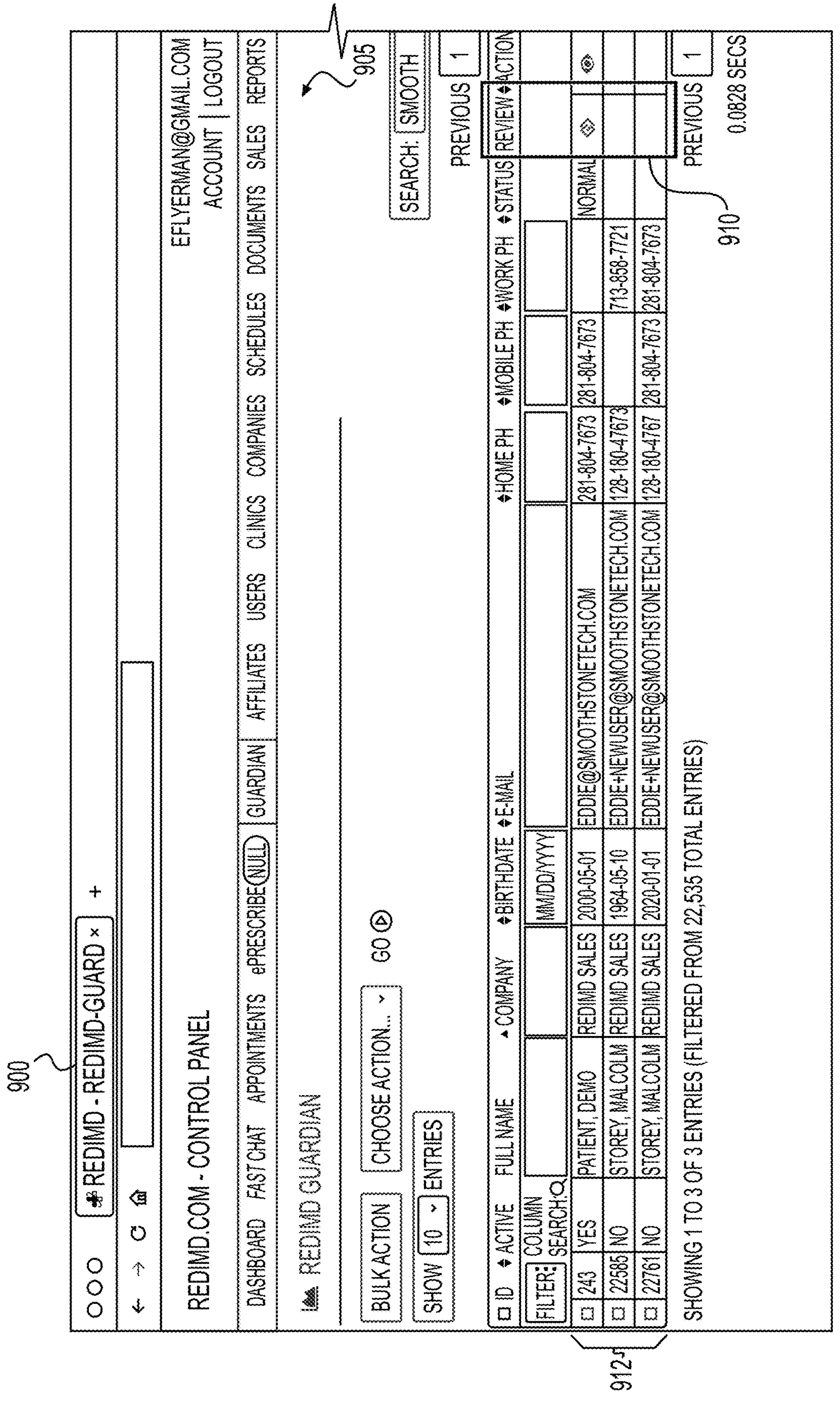

FIG. 9 shows an example of a page 900 that maybe displayed to an authorized user for administrative review. In this example, page 900 may include a display panel area 905 having a table of information relating to captured images and scan reading information determined by reader 116. This table may include an administrative review column 910 and multiple rows of entries 912. Each row corresponds to a user having a captured image, scanning reading information determined by reader 116, and other associated information. The administrative review column 910 may then include flags identifying whether a particular image or determined scanning reading information has been flagged for further administrative review. In this way, an administrator may review items flagged to further resolve and ensure correct sensor reading information is stored on health management platform 110 in database 130 even when reader 116 was unable to identify sensor reading information to a satisfactory level.

Online Application Operation with Health Management Platform

In one embodiment, a user (such as a patient) may navigate to a portal on the World Web Web and log in or follow the provided link in a reminder email or text message that includes a one-time-use token. An initial patient view is presented. The initial patient view may be a page 500 as shown in FIG. 5 having their historical data values presented in a line chart format. Clicking the add button 510 presents the patient with an input form 600 or 700 for entering data and a region for uploading an image of a device. Patients that use the provided link are taken directly to the input form 600 or 700.

The input fields and subsequent processes vary slightly dependent upon the type of monitoring the patient is enrolled. When the patient clicks the image region on a mobile device with a camera, the device's OS system may prompt the patient to take a photo or upload an existing file. In a browser, the patient can select an image to upload. Once an image is uploaded, the recognition process (e.g., step 240 described herein) begins automatically and may take about 1-2 seconds or less.

Once the recognition process is complete, the numeral values detected in the image are placed in the input fields in the input form (FIG. 8). The patient then has an opportunity to review and modify the input values provided by the recognition process before saving the observation to a database 130.

If the input values saved do not match the values detected during the recognition process or if the embedded timestamp of the image provided is more than 24 hours earlier or later than the observation timestamp, the observation is tagged with a "review" status. Healthcare providers can manually review observations tagged for review and resolve discrepancies (FIG. 9).

In a scenario where the digits from the image were not recognized correctly, the observation is left in a "review" status. Periodically the images from observations in a "review" status can be manually exported to another location for additional annotation and subsequent model training for evolutionary recognition improvement. Unique hash IDs (e.g., hash keys) are assigned to each image during the recognition process that allow the association of each observation to the results of each inference execution by ML engine 118. Using the hash id to map to individual observations to specific execution facilitates post execution issue resolution.

Example Implementation, Test Results and Training Data

Remote access to quality healthcare is crucial to saving lives. The recent Covid-19 pandemic has highlighted the need for leveraging A/ML for connecting with patients who require critical care. However, without access to proper diagnostic capabilities, medical practitioners are seriously handicapped. In examples, using state of art object detection techniques in ML engine 118 the inventors have been able to monitor patient vitals through images taken from smartphones.

In a further feature, this description illustrates not only a unique approach taken to solve this problem of connecting with remote patients in need of care, but also the creation of a unique training dataset to further help solve this problem. This dataset contains images of digital readings from a diverse set of medical devices. The inventors have been able to achieve 82% overall accuracy in a test dataset. This will enable medical professionals to leverage the latest object detection and recognition algorithms and remotely provide quality care.

In one example, a GUARDIAN application available from RediMD, LLC may be used in platform 110 for monitoring & management of blood glucose and blood pressure of individuals. Devices for measuring the two parameters, blood glucose and blood pressure, may include sensor devices such as the blood glucose and blood pressure monitors described in the "Blood glucose meter guide," *Diabetes UK*, Jan. 15, 2019 (last updated Jan. 7, 2022); and US Blood Pressure Validated Device Listing, www.validatebp.org (downloaded Mar. 16, 2022).

In embodiments, sensor devices having seven-segment displays may be used. Seven segment displays are made up of three horizontal and four vertically oriented segments. These can be turned on or off two display any of the ten digits. Seven segment displays are inexpensive and also easy to operate. The capability to read and infer readings from images these sensor devices enable health providers to remotely track their patients and provide them with quality care while still using more readily available and low-cost devices.

In tests, the inventors found a gap with existing computer vision tools like AWS Rekognition and GCP computer vision APIs. These platforms standing alone have difficulty in identifying seven-segment digits on LCDs. While a MNIST database described by Li Deng, "The MNIST database of handwritten digit images for machine learning research," *IEEE Signal Processing Magazine*, 29(6):141-142, 2012), was one of the first datasets used in computer vision problems, the inventors found these two existing APIs alone cannot distinctly detect seven-segment displays reliably. Previous research on this topic is also limited in the number and type of devices used for testing or has a complicated multi-step approach for identifying the region of interest and classifying the digits making them unworkable for telemedicine or remote health management.

Commercial Vision APIs Limits

Figure 10:
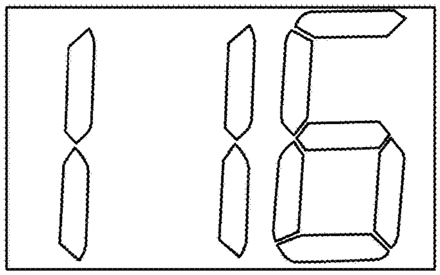
FIGS. 10-20 show example results of comparative tests according to an example implementation.
Figure 11:
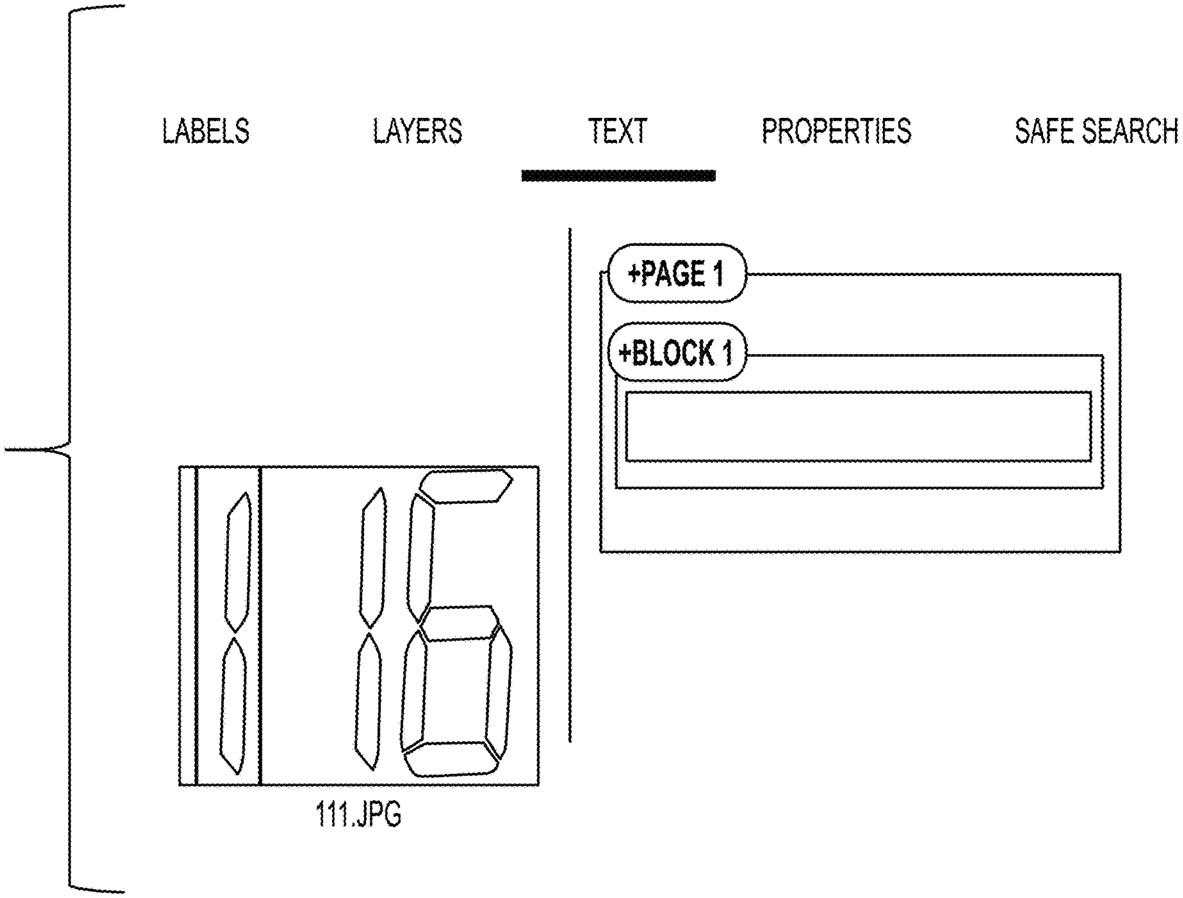

The inventors ran sample images of seven segment numeral displays through the following two commercially available APIs: AWS Rekognition API available from Amazon Web Services and Google Cloud Vision (GCP) Computer Vision API available from Google LLC. As shown in FIG. 10, the image has good clarity and the numbers are clearly visible, however AWS Rekognition API was not able to identify the text in the image. As shown in FIG. 11, GCP Computer Vision API was only able to detect the first one (1), since it draws a bounding box around it. However, it detects it as a curly bracket. Further tries were made with other sample images using both these APIs but the results were unsatisfactory.

Figure 12:
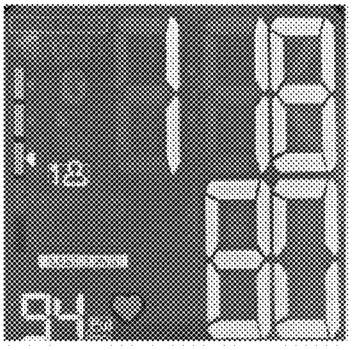
Figure 13:

In FIG. 12, both the APIs were unable to identify the seven segment numbers. As shown in FIG. 12, a sample image processed via AWS Rekognition API resulted in no digits detected. In FIG. 13, the AWS Rekognition API was able to identify some of the numbers from the image. This is seen from the bounding boxes. But again, the inventors found the output not satisfactory and the results not repeatable.

Test Results

The inventors describe computer-implemented methods and systems having an automated manner of identifying the region of interest and clustering the digits to achieve an overall accuracy of 82% on a test set.

Example ML Engine and Training Data

In one implementation to obtain test results, the inventors used a ML engine 118 having an object detection algorithm, loss function, and hyperparameter tuning as described herein. During training with training data, ML engine 118 trained an object detection algorithm to identify the digits and later cluster them on the basis of their bounding boxes. In one example the inventors used Detectron2 as described in Ross Girshick, Ilija Radosavovic, Georgia Gkioxari, Piotr Dollar, and Kaiming He, "Detectron" https://github.com/facebookresearch/detectron, 2018) which is a ground-up rework of Detectron. Underneath the algorithm according to an embodiment uses Faster-RCNN for object detection. See, Ren, S., He, K., Girshick, R. B., & Sun, J. (2015), "Faster R-CNN: Towards Real-Time Object Detection with Region Proposal Networks," *IEEE Transactions on Pattern Analysis and Machine Intelligence*, 39, 1137-1149.

The inventors in an example implementation used advanced augmentation strategies for creating synthetic data for a training dataset. Details of the training dataset and the augmentation strategies is explained in the Dataset Details section below.

The inventors also used an edge-deployment for the model in an embodiment. This meant that the model should be trained with a backbone which is small in size and can run on a processor (CPU), with low latency and high accuracy. In this embodiment, the inventors use D2go which is a deep-learning toolkit powered by PyTorch and Detectron2 available from Facebook Research. See, Ross Girshick, Ilija Radosavovic, Georgia Gkioxari, Piotr Dollar, and Kaiming He, *Detectron*, https://github.com/facebookresearch/detectron, 2018. This provides a state-of-art efficient backbone networks for mobile deployment. Along with end-to-end model training, quantization and deployment pipelines. It also has libraries to export the model to TorchScript format for deployment. Model quantization and deployment as an API is further described in the Quantization and Model Deployment section below.

Object Detection

Figure 14:
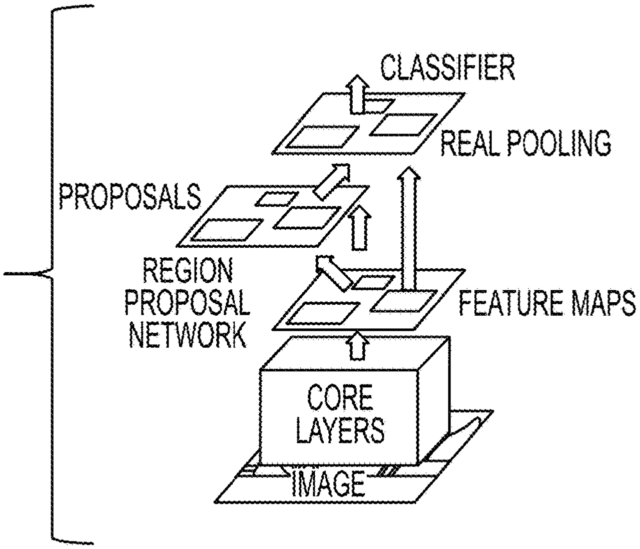

The inventors used Faster-RCNN which is a single unified neural network for object detection. See, Shaoqing Ren, Kaiming He, Ross B. Girshick, and Jian Sun. *Faster R-CNN: towards real-time object detection with region proposal networks*, CoRR, abs/1506.01497, 2015. As shown in FIG. 14, an image is passed to the Faster-RCNN. The Faster-RCNN includes core layers that analyze the image and obtain feature maps. The feature maps are used by a Region Proposal Network (RPN) to obtain proposals. In this way, the RPN serves as the attention mechanism for the neural network. The feature maps and proposals are output to a classifier. Region of Interest (ROI) pooling is used to allow a single feature map for all the proposals generated by RPN in a single pass. In this way, ROI pooling solves the problem of a fixed image size requirement for the object detection network.

The object detection used employed a combination of two losses, the first is detecting the bounding boxes (regression) around the object of interest, the second is classifying the boxes into a specific category. So the loss function (L or Loss) can be defined as:

$$\text{Loss} = \text{Loss}_{class} + \text{Loss}_{reg}$$

which basically results in the following equation—

$$L(p_i, t_i) = \frac{1}{N_{cls}}\sum_i L_{cls}(p_i, p_i^*) + \lambda\frac{1}{N_{reg}}\sum_i p_i^* L_{reg}(t_i, t_i^*)$$

where i: index of anchor $p_i$: predicted probability $p^*_i$: ground truth label=1 if positive else 0

$t_i$: vector representing the parameterized coordinates of the predicted bounding box $t^*_i$: ground-truth box associated with a positive anchor and where Loss: total loss $\text{Loss}_{(class)}$ or $\text{Loss}_{(cls)}$: classification loss $\text{Loss}_{(reg)}$: regression loss $N_{(class)}$, $N_{(reg)}$ are normalization terms for the losses $N_{(class)}$ or $N_{(cls)}$: mini-batch size $N_{(reg)}$: number of anchor locations λ: balancing weight.

Hyperparameter Tuning

Figure 15:
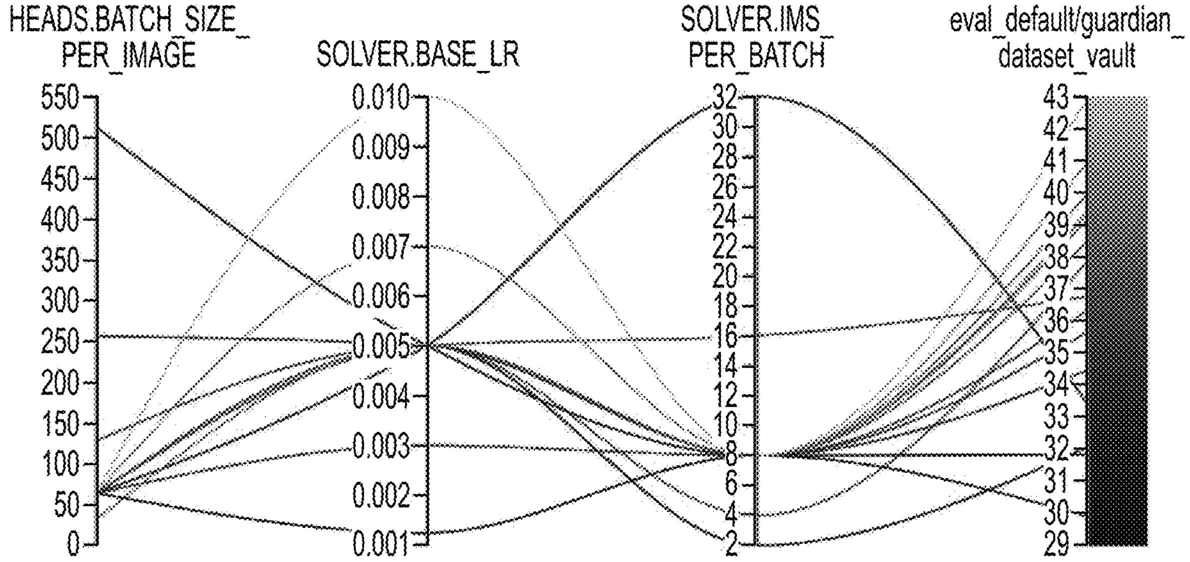

The inventors used a tool Wandb available from Weights & Bases (https://wandb.ai/site) for visualization and hyper-parameter tuning of model parameters. FIG. 15 shows diagrams of hyperparameter sweeps obtained using the Wandb tool. The inventors also automated hyperparameter optimization and explored the space of possible models in an example implementation. A batch size of 64, with ims batch size of 8 was found to be optimal for training the model. Increasing batch-size and training the model for higher number of iterations with an augmented dataset, improves the accuracy of the model.

The inventors also examined the effect of updating the normalization parameters. Normalization of image pixel values is also one of the major steps during model training. Normalization ensures that there is optimal training of the neural network. However, the model uses the mean & std-dev parameters as calculated from the ImageNet dataset. See, Jia Deng, Wei Dong, Richard Socher, Li-Jia Li, Kai Li, and Li Fei-Fei, "Imagenet: A large-scale hierarchical image database," 2009 *IEEE Conference on Computer Vision and Pattern Recognition*, pages 248-255, 2009. The ImageNet dataset is organized according to the WordNet hierarchy. There are more than 100k synonym sets with 1000 sample image for each synonym set. However, these images vary considerably with the images that that this model will process. In a further feature, the inventors updated the model parameters, mean and std-deviation, with the mean values from a collated dataset. This has shown a considerable improvement in the precision (validation) for the model.

Dataset Details

Figure 16:
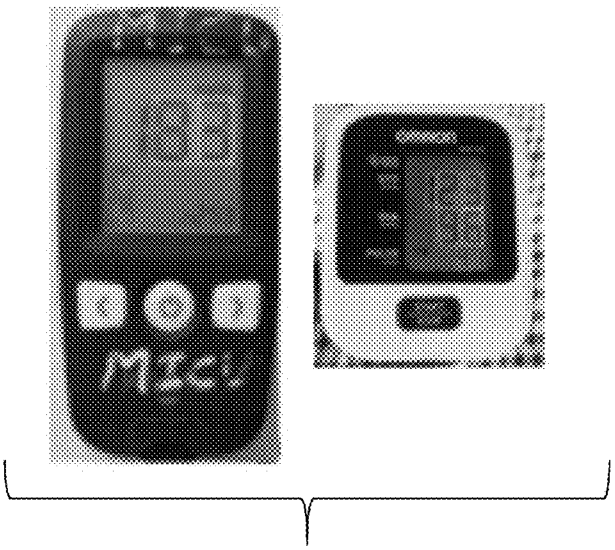

The inventors addressed these issues in the tests while collecting observations from multiple sensor devices. The dataset was collected via paid volunteers who were asked to take images using different backgrounds, orientations and lighting conditions. This also gives a diversity of devices. FIG. 16 shows sample images with annotations. The preferred measurement unit for blood sugar varies by country: mg/dl are preferred in the U.S., France, Japan, Israel, and India. mmol/l are used in Canada, Australia, China, Malaysia and the UK. The inventors have sourced blood sugar readings with both unit types. To address privacy concerns, all exif information was stripped from the training dataset images. No information of the paid volunteers was stored with the dataset.

Data Distribution

Tables 1 and 2 show further information on the distribution of images and sensor device readings used. As can be seen, there is a balanced distribution between images of glucometer and bp-monitors (see Table 1). The distribution of images between a train and validation dataset is done via a 90:10 split. However due to the nature of the readings, few of the digits have a higher probability of occurrence in any observation. Table 2 shows that the frequency of ones(1) and eights(8) is 4×-3× the lower probability digits like fours(4) and threes(3). This creates some unbalance in the annotations.

TABLE 1

| Distribution of images | |
|---|---|
| Name | Count |
| Glucometer | 527 |
| BP Monitor | 608 |
| Total | 1,135 |

TABLE 2

| Distribution of digits | |
|---|---|
| Name | Count |
| Zero | 606 |
| One | 1,407 |
| Two | 455 |
| Three | 381 |
| Four | 432 |
| Five | 688 |
| Six | 888 |
| Seven | 919 |
| Eight | 1,175 |
| Nine | 541 |
| Total | 7,492 |

The dataset used in the example for training and validation is proprietary and not publicly available. Annotations are available in the following formats: COCO; YOLO; PASCAL VOC and TFRECORDS. This makes it easier for a machine learning engineer to switch between any deep learning framework of choice.

Data Augmentations

The inventors further used data augmentation to increase training data size and increase number of annotations. Data augmentation is a set of techniques that can be used to enhance the size and quantity of training datasets such that Deep Learning models can be built using them. Data augmentation can be considered as a data-space solution to the problem of limited data. The augmentation techniques that were used by inventors for the test of ML engine 118 include geometric transformations, color space augmentations, kernel filters, noise injection, cropping, mixing images as in Yun et al. (Sangdoo Yun, Dongyoon Han, Seong Joon Oh, Sanghyuk Chun, Junsuk Choe, and Youngjoon Yoo, "Cutmix: Regularization strategy to train strong classifiers with localizable features," *International Conference on Computer Vision* (*ICCV*), 2019) and Zhang et al. (Hongyi Zhang, Moustapha Cisse, Yann N. Dauphin, and David Lopez-Paz. "Mixup: Beyond empirical risk minimization," *International Conference on Learning Representations,* 2018, random erasing Devries et al. (Terrance DeVries and Graham W Taylor, "Improved regularization of convolutional neural networks with cutout," *arXiv preprint arXiv:*1708.04552, 2017), adversarial training, GANs and neural-style transfer (Ren Wu, Shengen Yan, Yi Shan, Qunigqing Dang, and Gang Sun, "Deep image: Scaling up image recognition. *CoRR*, abs/1501.02876, 2015." Withdrawn.).

The inventors recognized one or more of the following augmentations can be used: Horizontal Flip, Vertical Flip, Shift-Scale-Rotate, Random-Brightness-Contrast, Random Sun Flare, Random Fog, Blur, CLAHE, Downscale, Perspective, Sharpen, Gaussian Blur, Gaussian Noise, Multiplicative Noise, Cutout, Random Sized BBox SafeCrop, CutMix, or MixUp.

FIG. 17 shows eight base augmentations of an original which were used in one example. The base augmentations of the original ("Original") shown in FIG. 17 are Random Fog, Random-Brightness, Random Crop, Rotate, RGB-Shift, Random Snow, Vertical Flip, and Random Contrast. The original and base augmentations were chained together to generate a large synthetic training dataset. Some part of the annotation can be lost after a chain transformation. So, post the operation, if only less than 40% of the original annotations are available, then that transformation is rejected. This loss is visible in the RandomCrop transformation for example shown in FIG. 17. These eight base augmentations are illustrative and not intended to be limiting and a fewer or larger number of augmentations of different types may be used.

Figure 18:
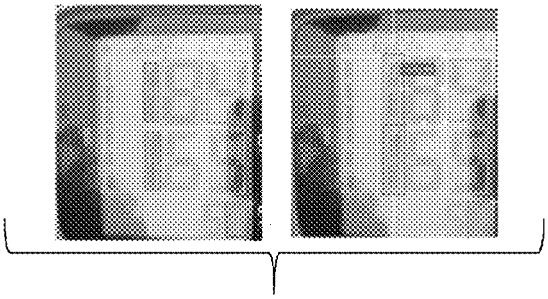
Figure 19:
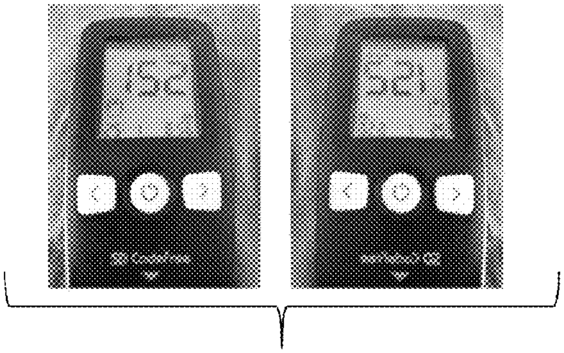
Figure 20:
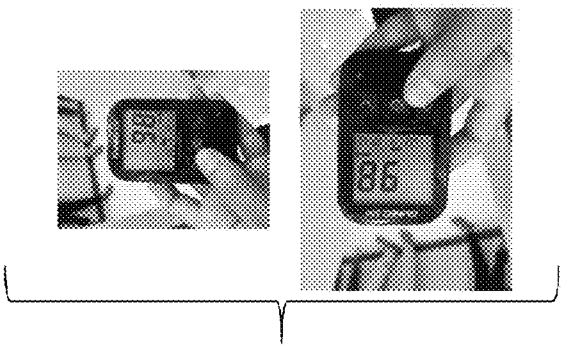

In the test, there were some idiosyncrasies unique to the training dataset. Since the digits are formed from seven-segments, data augmentation should be properly monitored. FIGS. 18-20 show special cases or exceptions which are managed during augmentation. Here is a list of criteria used in obtaining a trained model 122 below:

Ones (1) are built using two vertical segments, hence they are part of any of the following digits—three (3), six (6), seven (7), eight (8—two vertical lines), nine (9) and zero (0—two vertical lines). This makes it difficult to recognize—even though it's the largest annotated label (See FIG. 18);

Twos (2) and fives (5) appear the same when flipped on the vertical axis or horizontal axis (See FIG. 19); and Nines (9) and sixes (6) will appear the same when flipped on the vertical (See FIG. 20).

Since the ones are part of a number of seven-segment digits (three, six, seven, eight, nine and zeros) they require special treatment during annotation. The inventors increased the bounding box rectangle around the ones to distinguish them from vertical segments appearing in any other digits. FIG. 18 shows an example of increasing the size of bounding box for ones used in modifying annotation. The left image in FIG. 18 illustrates the bounding box around ones while the right image illustrates the bounding box having increased size for ones.

For the other pairs, such as two-five and six-nine, during augmentation the inventors avoided any kind of flips or rotations in the test. FIG. 19 illustrates how due to a horizontal flip, a two is converted into a five while a five is converted to a two.

A combination of flips, horizontal and vertical may also change a reading from—98 to 86. This is seen in FIG. 20 which shows how vertical flipping changes nines to sixes and vice versa.

Quantization and Model Deployment

In further examples, the following may be used in a quantization of a model a) lambda deployment; b) containerized images; c) use of S3 buckets for storage; d) automated reporting & model tracking.

In this example implementation, the inventors demonstrate a unique approach to detect and identify readings from seven-segment displays. A computer-implemented described herein achieved an overall accuracy of 82% in tests which is higher than the current published research. To achieve this benchmark, the inventors have also collected a dataset of more than 1100+ sample images, which are taken in real-life settings.

FURTHER EMBODIMENTS AND EXAMPLE IMPLEMENTATIONS

Various embodiments can be implemented on client and server sides, for example, using one or more computing devices at the same or different locations. A computing device (such as computing device 150 or computing devices implementing platform 110) can be any type of device having one or more processors and memory. For example, a computing device can be a workstation, mobile device (e.g., a mobile phone, personal digital assistant, tablet or laptop), computer, server, computer cluster, server farm, game console, set-top box, kiosk, embedded system, or other device having at least one processor and computer-readable memory. In addition to at least one processor and memory, such a computing device may include software, firmware, hardware, or a combination thereof. Software may include one or more applications and an operating system. Hardware can include, but is not limited to, a processor, memory and user interface display or other input/output device.

Aspects of computing embodiments on client and server sides (including computing device 150 and platform 110) may be implemented electronically using hardware, software modules, firmware, tangible computer readable or computer usable storage media having instructions stored thereon, or a combination thereof and may be implemented in one or more computer systems or other processing systems.

Embodiments are also directed to computer program products comprising software stored on any computer-usable medium. Such software, when executed in one or more data processing devices (such as a processor), causes a data processing device(s) to operate as described herein or, as noted above, allows for the synthesis and/or manufacture of electronic devices (e.g., ASICs, or processors) to perform embodiments described herein. Embodiments employ any computer-usable or -readable medium, and any computer-usable or -readable storage medium known now or in the future. Examples of computer-usable or computer-readable mediums include, but are not limited to, primary storage devices (e.g., any type of random-access memory), secondary storage devices (e.g., hard drives, floppy disks, CD ROMS, ZIP disks, tapes, magnetic storage devices, optical storage devices, MEMS, nano-technological storage devices, etc.), and communication mediums (e.g., wired and wireless communications networks, local area networks, wide area networks, intranets, etc.). Computer-usable or computer-readable mediums can include any form of transitory (which include signals) or non-transitory media (which exclude signals). Non-transitory media comprise, by way of non-limiting example, the aforementioned physical storage devices (e.g., primary and secondary storage devices).

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed. The breadth and scope of the present invention should not be limited by any of the above-described exemplary embodiments.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What is claimed is:

1. A computer-implemented system for numeric character recognition of numerals shown in a segmented display on a sensor device over a data network, comprising:
means for capturing a digital image of a segmented display of numeric values shown on a sensor device;
means for sending the digital image to a remote health management system having a reader;
means for storing the digital image in a computer-readably memory; and
means for processing the digital image at the reader to determine a sensor reading representative of the numeric values in the segmented display of the sensor device, wherein the processing means includes:
means for analyzing the digital image using optical character recognition to determine a first array of data;
means for analyzing the digital image using a trained machine learning (ML) model to determine a second array of data; and
means for evaluating the first and second arrays of data to obtain the sensor reading representative of the numeric values in the segmented display of the sensor device.

2. The computer-implemented system of claim 1, wherein the segmented display comprises a seven-segment display where seven segments are displayed on or off to represent particular numeric values between 0 and 9.

3. The computer-implemented system of claim 1, wherein the processing means includes means for identifying a region of interest and clustering digits.

4. The computer-implemented system of claim 3, wherein the identifying a region of interest means includes means for object detection.

5. The computer-implemented system of claim 1, further comprising means for training a model having parameters, and wherein the processing means includes means for minimizing a loss function and hyperparameter tuning of parameters in the model.

6. The computer-implemented system of claim 1, wherein the evaluating means includes:
means for comparing the first and second arrays of data to determine whether data in the first and second arrays is identical or empty;
means for outputting an output array of data having data from the first or second array of data when identical and from the first or second array that is not empty; and
means for arbitrating the first and second arrays of data according to test criteria to obtain an output array of data when the comparing means determines the first and second arrays of data are not identical and empty.

7. The computer-implemented system of claim 6, further comprising means for temporarily saving the obtained output array of data in computer-readable memory along with an identifier associated with the digital image.

8. The computer-implemented system of claim 1, further comprising:
means for displaying the sensor reading information as numeric values along with the associated digital image for confirmation; and
means for enabling a user to edit or select the numeric values and submit an input indicative of user confirmation.

9. The computer-implemented system of claim 8, further comprising:
means for comparing the user confirmation input and the temporarily saved output array of data;
means for checking whether the comparison is passed or not passed;
means for flagging the sensor reading information of the output array of data for administrative review when the comparison is not passed; and
means for saving the sensor reading information of the output array of data in a record of a database.

10. The computer-implemented system of claim 1, further comprising means for training the ML engine with a training dataset of images to obtain the trained ML model.

11. The computer-implemented system of claim 10, wherein
the training dataset includes base images of different sensor reading devices having segmented numeral displays, and the training means includes:
means for augmenting base images in the training dataset to generate a synthetic training dataset that includes base augmentations representative of one or more of the following augmentations: Horizontal Flip, Vertical Flip, Shift-Scale-Rotate, Random-Brightness-Contrast, Random Sun Flare, Random Fog, or Blur of each base image in the training dataset.

12. The computer-implemented system of claim 10, wherein
the training means includes:
means for applying images in the training dataset to a ML engine;
means for evaluating candidate models using objection detection,
means for minimizing a loss function and hyper-parameters to obtain the trained ML model.

13. The computer-implemented system of claim 1, wherein the analyzing means for the digital image using the trained ML model includes means for passing to the digital image with an API call to a Detectron2Go library to determine the second array of data.

* * * * *